United States Patent [19]

Lefrancier et al.

[11] 4,396,607

[45] Aug. 2, 1983

[54] MURAMYL PEPTIDE DERIVATIVES AND PHARMACEUTICAL COMPOSITIONS

[75] Inventors: Pierre Lefrancier, Bures sur Yvette; Monique Parant, Paris; Francoise Audibert, Neuilly sur Seine; Edgar Sache, Bures sur Yvette; Louis Chedid; Jean Choay, both of Paris; Edgar Lederer, Sceaux, all of France

[73] Assignee: Agence Nationale de Valorisation de la Recherche (ANVAR), Neuilly sur Seine, France

[21] Appl. No.: 259,450

[22] Filed: May 1, 1981

Related U.S. Application Data

[63] Continuation of Ser. No. 105,528, Dec. 20, 1979, abandoned.

[30] Foreign Application Priority Data

Mar. 20, 1978 [FR] France ............................. 78 08049
Nov. 13, 1978 [FR] France ............................. 78 33126

[51] Int. Cl.³ .................. A61K 37/00; C07C 103/52; A61K 39/00
[52] U.S. Cl. ............................. 424/177; 260/112.5 R; 424/85; 424/88
[58] Field of Search .................. 260/112.5 R; 424/177, 424/85, 88

[56] References Cited

U.S. PATENT DOCUMENTS 4,153,684  5/1979  Audibert et al. ............ 260/112.5 R

FOREIGN PATENT DOCUMENTS 3833    2/1979  Fed. Rep. of Germany ... 260/112.5 R
201534A 2/1979  United Kingdom ............. 260/112.5 R

OTHER PUBLICATIONS

Chem. Abstr. vol. 88, 1978, p. 136983x.

*Primary Examiner*—Delbert R. Phillips
*Attorney, Agent, or Firm*—Weiser, Stapler & Spivak

[57] ABSTRACT

The invention relates to new compounds useful notably as regulator of immune responses and which are derivatives of muramyl peptides substituted at the end of the peptide chain by a group containing at least four carbon atoms.

49 Claims, No Drawings

MURAMYL PEPTIDE DERIVATIVES AND PHARMACEUTICAL COMPOSITIONS

This is a continuation of application Ser. No. 105,528, filed Dec. 20, 1979, now abandoned.

The invention relates to novel products endowed with biological and pharmacological properties of great value, which can be utilized in connection with standardized laboratory reactants for the comparative study of similar biological properties of other compounds, or as a compenent of novel medicaments for human or veterinary use.

The invention relates more particularly to novel products capable of modifying the immune responses in warm-blooded animals. More specifically, it relates to novel products capable of stimulating the immune responses which bring into play at least one and preferably all of the mechanisms constituting the humoral immune response support (opsonins, antibodies) or the cell mediated immune response. These mechanisms may be specific (their intervention depending on prior vaccination by a given antigen mixture, and more particularly derived from pathogenic agents), or non-specific (such as are induced by agents such as BCG, corynebacteria or endotoxins).

It is known that organisms of warm-blooded animals comprise several types of cells constituting what could be called several lines of defense with respect to the various aggressions to which these organisms may be subject.

The first line of defense brings into play, as is well-known, the leucocytes and macrophages in the blood stream which are, capable, when they encounter a foreign agent such as an antigen, of phagocyting it and often of destroying it. This phagocytosis can be facilitated notably by non-specific constituents of the serum (opsonins), even by external interventions leading to activation of the macrophages.

A second line of defense of the organism brings into play mechanisms triggered by antigenic constituents of the foreign agent. These immune mechanisms bring into play cellular differentiations in at least one of the two following principal directions.

A first type of immune mechanism brings into action specialized cells (B lymphocytes) which are precursors of the cells which secrete immunoglobulins or antibodies. These immunoglobulins or antibodies play an important role in the battle against infection caused by bacteria or other micro-organisms which replicate in the humoral fluids, or to neutralize toxins or the like. With this type of action, specific to the antigen concerned, is added an indirect action by circulating mediators, which are manifested by activation of the cells responsible for phagocytosis, thus reinforcing the non-specific defenses of the organism.

The second type of immune mechanism brings into play specifically sensitized cells belonging to the lymphocyte line (T cells), which interact on the previously indicated B cells, or on the macrophages leading to activation of the latter or of other non-specific cells.

In the face of these various mechanisms presented diagrammatically below, it is possible to distinguish two types of infectious according to the manner in which they develop and the mechanisms which are obliged to combat them. Thus, for certain infections, a simple phagocytosis, facilitated possibly by specific humoral or non-humoral factors, permits the destruction of the infectious agents. For other types of infections, phagocytosis is not sufficient.

The phagocyted infectious agent is not destroyed and even continues to act within the phagocyting cell, resulting on the contrary in the destruction of the latter. In this case, to prevent intracellular growth of the infectious agents, it is necessary to "activate" the phagocyting cells according to the above-indicated processes.

When it is desired to study the anti-infectious properties of novel products, the Klebsiella, as infecting strains with extracellular replication, are particularly representative. These bacteria have in fact a capsule of large size which only permits effective phagocytosis by macrophages. Through the mechanism of applying non-specific agents, the results obtained with Klebsiella may be extended to micro-organisms which replicate in the same manner.

An experimental procedure was studied by CHEDID L. et col. in "Proc. Natl. Acad. Sci." USA, 1977, 74: 2089, which permits the presence of absence of stimulating effect to be observed of substances studies with regard to immune defenses as they protect or not the mice to which they are injected, the mice being inoculated by a dose of *Klebsiella Pneumoniae* which results in the death of almost all of the controls.

When it is desired to study the effects of such substances on infections whose agents multiply intracellularly, the Listeria are among the micro-organisms most used, and notably *Listeria monocytogenes*. The latter are the basis of biological tests which have become classical, both for the study of specific and non-specific reactions.

By way of example, may be mentioned the experimental procedure described by MEDINA, VAS and ROBSON (J. Immunol., 1975, 114, 1720), which permits the stimulant or non-stimulant effect to be observed of substances studied with regard to immune defenses, as they protect or not mice into which they are injected against a dose of *Listeria monocytogenes* which results in the death of almost all of the controls, or as they result or not in the short-term destruction of said micro-organisms.

It is more and more confirmed today that cell mediated immunity constitutes a complex defense system of organisms coming into play in numerous situations, not only with respect to intracellular micro-organisms but also with respect to neoplastic growth and the multiplication of numerous fungal, parasitic agents, etc.; it is this system which is also responsible in the rejection of grafts and numerous auto-immune processes.

In a general way, reference may be made, as regards all of the above-mentioned problems, to, for example, the articles of Priscilla A. CAMPBELL, entitled "Immunocompetent Cells in Resistance to Bacterial Infections", which appeared in "Bacteriological Reviews", June 1976, p. 284–313, of G. B. MACKANESS, entitled "Cellular Immunity", which appeared in the Annals of the Pasteur Institute, 1971, 120, 428–437, of G. H. WERNER et coll., entitled "Toxicological Aspects of Immunopotentiation by Adjuvants and Immunostimulating Substances", which appeared in the Bulletin of the PASTEUR INSTITUTE, volume 75, No. 1 of January 1977, and in a report of a scientific group of the World Health Organization, entitled "Reponses immunitaires a support cellulaire", which appeared in "Org. mond. Sante, Ser. Rapp. tech.," 1969, No. 423.

It is apparent from the foregoing that the placing at the disposal of specialists, notably of the biologist and the clinician, of compositions or products capable of stimulating immunitary defenses of the above-indicated types, can have capital importance both for the study of other substances at the research level, both fundamental and applied, and in the domain of human or veterinary therapeutics.

Certain agents are already known which are capable of stimulating non-specifically these various immunitary responses, both for cellular mediation and for humoral mediation. Thus, for example, bacterial lipopolysaccharides (LPS), are known for their protective activity with respect to humoral or cellular infections. The LPS possess, in addition, non-specific immunological adjuvant properties, in that they facilitate an increase in the ratio of specific antibody synthesis by an organism subjected to antigen aggression, of any nature.

It is known in the same way that mycobacteria, and more particularly "Calmette-Guerin bacillus" (CGB), possess powerful non-specific immunostimulating properties.

However, there can be no question of contemplating the utilization of LPS in therapeutics, considering their extreme toxicity which is well known. CGB itself is not free of numerous drawbacks, which can be demonstrated, for example, in the animal, notably at the level of the increase in sensitivity of the host to endotoxins, of the production of a hypersensitivity to tuberculin, of the induction of granuloma, of hyperplasia of the lymphoid tissue and, notably in the rat, of polyarthritis.

It is known that numerous researchers are attached to the study of extracts capable of being obtained from mycobacteria, for the purpose of obtaining purified or detoxified agents retaining the biological properties of value of CGB or LPS, whilst being free of the above-mentioned drawbacks. The development of these researches has led to small molecules, representing in themselves a considerable contribution to the arsenal of substances which the researcher and clinician has available. These substances which are now acceptable in chemical synthesis, which are practically devoid of toxicity and whose very powerful immunological adjuvant activity, are manifested even when they are administered to a host, in the absence of a oily support, as was necessary as regards more particularly the fractions obtained by extraction, notably from mycobacteria.

The above-said small molecules are, as is now well known, constituted by N-acyl-muramyl-peptides or certain of their substitution derivatives, characterized by an N-acyl-muramic group to which is attached a peptide chain comprising a first aminoacyl residue directly linked to the N-acyl-muramic acid, constituted by a glycyl residue, or a derivative of another levogyro amino acid, preferably an L-alanyl or L-seryl residue, and a second aminoacyl group, linked to the first, derived from D-glutamic acid.

The most active products as immunological adjuvants are constituted by the N-acetyl-muramyl-peptides, whose first aminoacyl residue is a L-alanyl or L-seryl and the second a D-glutamyl residue whose $\gamma$ carboxyl function may be either free, or esterified or amidated (the amide group being itself capable of carrying substitution groups) and whose $\gamma$ carboxyl function may also be either free or amidated or esterified, or again enters a longer peptide chain. The most representative product of the series of N-acyl-muramyl-peptides is constituted by N-acyl-muramyl-L-alanyl-D-isoglutamine (MDP). Various researches have however shown that the immunological adjuvant activity could be maintained, to a greater or lesser extent, by the introduction of various substitutions into the muramyl group or by the replacement of the first amino-acyl residue by others, derived from various amino acids of the L-series.

It has already been observed for certain of the muramyl-peptides of the type concerned, and more particularly as regards N-acetyl-muramyl-L-alanyl-D-isoglutamine already mentioned (MDP) or for the corresponding non-amidated derivative, namely N-acetyl-muramyl-L-alanyl-D-glutamic acid (MDPA) or again $\alpha$-esters of MDPA, that they possessed in addition, very considerable anti-infectious properties, which are manifested more particularly with micro-organisms with humoral multiplication (Klebsiella).

The invention arises from the discovery that introducing a lipophilic chain (that is, an essentially non-polar hydrocarbon chain), to the $\gamma$—carboxylic function of the glutamyl residue led to the production of a novel category of derivatives of the muramyl-peptide type characterized notably by powerful anti-infectious activity. It will be observed that the fixing of the lipophilic chain on to the peptide chain, which characterizes the novel products according to the invention, goes entirely contrary to what it has been possible to observe in water-soluble adjuvant natural products which can be produced from cellular walls of micro-organisms, such as mycobacteria, and which include in their structure at least one peptidoglycan fragment. In fact, certain of these natural products can include lipophilic chains fixed indirectly to certain saccharide units of the peptidoglycan, but have never been found on the peptide chains of the latter.

The different properties of the products according to the invention and more particularly their anti-infectious properties are in addition all the more unexpected as the short $\gamma$-monoesters of the MDPA do not possess anti-infectious properties with regards to the humoral immunitary defense mechanism.

Products according to the invention demonstrate in addition a new advance with respect to products already known, in that they show themselves to be capable not only of exerting a non-specific stimulating effect of the humoral immunitary defenses, but also of cell mediated immunity.

The novel compounds according to the invention correspond to the general formula

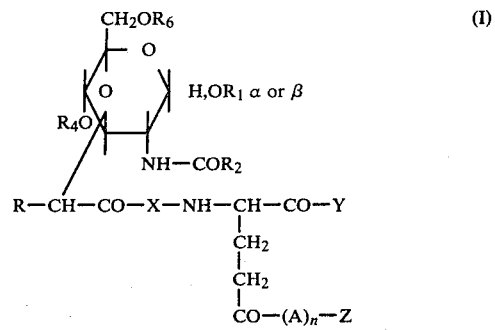

in which the constituents R, $R_1$, $R_2$, $R_4$, $R_6$, X, Y and Z have the following significances:

R is preferably either a hydrogen atom, or an alkyl group comprising 1 to 4 carbon atoms, $R_1$ is preferably a hydrogen atom, an alkyl group having preferably at the most 4 carbon atoms, a simple or substituted aryl or alkyl-aryl group comprising preferably at the most 10 carbon atoms, $R_2$ is preferably an hydrogen atom or an alkyl or alkyl-aryl group possibly substituted by groups not modifying the characteristics of the product and including preferably at the most 22 carbon atoms, $R_4$ is a hydrogen atom, an acyl radical comprising preferably at the most 4 carbon atoms, $R_6$ is preferably a hydrogen atom, or an acyl radical, saturated or not, possibly branched, containing from about 1 to 90 carbon atoms, and which can in addition carry functional groups: hydroxyl carboxyl, carbonyl, amino, cyclopropane, alkoxy (preferably methoxy), X is an aminoacyl residue of the group comprising: L-alanyl, L-arginyl, L-asparagyl, L-aspartyl, L-cysteinyl, L-glutaminyl, L-glutamyl, glycyl, L-histidyl, L-hydroxyprolyl, L-isoleucyl, L-leucyl, L-lysyl, L-methionyl, L-ornithyl, L-phenylalanyl, L-propyl, L-seryl, L-threonyl, L-tryptophanyl, L-tyrosyl and L-valyl, Y is either -OH, or an alkoxy radical comprising from 1 to 10 carbon atoms, or $-NH_2$, the hydrogens of the amino group being capable of being substituted by alkyl residues of 1 to 10 carbon atoms, or an aminoacyl residue, A is an aminoacyl residue of the group indicated above for X, or, for the last of the peptide chain, an aminoalcohol residue

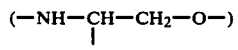

$(-NH-CH-CH_2-O-)$ corresponding to the aminoacyls

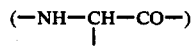

$(-NH-CH-CO-)$ it being understood that the A groups present in the same compound may be identical or different, n only representing the total number of A groups in this compound, n is zero or 1, 2 or 3, Z is a group -OR', -NHR', $-OCH_2-CH_2O-COR'$ or $-OCH_2-CHOH-CH_2O-COR'$ when the last A residue of the peptide chain is an aminoacyl, and -COR' when this last A is an aminoalcohol, in which R' is a linear or branched alkyl saturated or not, and can contain functional groups hydroxyl, carbonyl, carboxyl, cyclopropane, aryl, the latter being possibly substituted, this group comprising at least 4 carbons and being able to include up to 90 carbon atoms.

In this formula, the second aminoacyl group of the peptide chain connected to the group of the muramyl type is the D-glutamyl residue. The first aminoacyl group (denoted by X) may, on the other hand, be selected from among the various aminoacyl groups mentioned above. Among the compounds of formula (I) those are preferred in which the first aminoacyl group is L-alanyl, a second type of preferred compound is that in which this aminoacyl is L-seryl, another type of preferred compound is that in which the aminoacyl is the glycyl group.

Also advantageous are the compounds in which the first aminoacyl group is L-prolyl, L-threonyl or L-valyl.

The substituents at the γ position of the glutamyl residue all have in common a hydrocarbon group R' of which a feature is that on the whole, whatever the exact structure of this group, it has a tendency either to confer a certain lipophilic character on the compound concerned, or to increase this character when, independently of the R' group, it is already manifested.

The lipophilic character of the hydrocarbon groups corresponding to the definition of R' increases quite obviously with the number of the carbon atoms of the group when one starts from the shortest substituents, that is to say, in the present case, the groups R' having 4 carbon atoms.

In theory, the number of carbon atoms comprised in R' is not limited upward. Nonetheless, in practice, the increase in the number of carbon atoms, beyond a certain threshold, does not contribute advantages and necessitates the application of reactants which are difficult to obtain commercially. In practice, the group R' does not contain more than a certain number of carbon atoms, and preferably not more than 90. The lipophilic character reaches an advantageous level as soon as R' contains about ten carbons.

Between the D-glutamyl residue and the group R' may be inserted one or several additional aminoacyl residues denoted in the general formula by A.

Preferably, these aminoacyls are selected from the group comprising: alanyl, leucyl, lysyl, glycyl, valyl, glutamyl and isoleucyl.

In particularly preferred manner, the first aminoacyl fixed at the γ of the D-glutamyl is L-alanyl. Also by preference, this aminoacyl is L-lysyl or L-glutamyl.

The number of aminoacyls between the D-glutamyl and the R' group may vary from 0 to 3, preferably however it is either 0, or 1, or 2.

If necessary, the last aminoacyl can be replaced by the aminoalcohol residue of the same carbon structure as the aminoacyl, the linkage with the R' group then taking the form of an ester of this aminoalcohol with an acyl —CO—R'.

At the α position of the D-glutamyl residue, the modifications or possible substitutions are more limited than at the γ position of this same group. The Y substituent can firstly represent the —OH radical, that is to say that the carboxylic function of glutamic acid again occurs. It can also be the amide form of this acid, that is to say the isoglutaminyl form, Y being $-NH_2$, one at least of the hydrogen atoms of the amino group being capable of being substituted by short alkyl residues comprising from 1 to 10 carbon atoms. It can again be esterified forms of the acid, Y then being an alkoxy, comprising from 1 to 10 carbon atoms.

In a preferred form, Y is a hydroxyl.

In another preferred form, Y is $-NH_2$.

Another preferred form is constituted by the case where Y is either $-OCH_3$, or $-OC_2H_5$.

In the most customary preferred form, that is to say that corresponding to the muramic acid structure, R is $-CH_3$. In another preferred form, the group R is hydrogen; the structure of the lower homologue denoted by the name nor-muramic acid is then found. Finally, in another preferred form, R is $-C_2H_5$; the so-called homomuramic structure corresponds to this form.

The glycoside linkage of the saccharide portion in the products according to the invention can be present in α or β form. The osidic residue can also receive different substituents of which the prior literature relating to adjuvant agents of muramyl-peptide type, has given a certain number of examples. In particular, the literature describes products whose functional groups of the osidic residue are "blocked" by the formation of ester or ether groups on the hydroxyls, or of amide groups on the amino radical at the 2 position.

In the general formula of the products according to the invention, the substituents of the glucopyranoside cycle have been denoted by $R_1$, $R_2$, $R_4$ and $R_6$. The various positions do not present the same possibilities of substitution, the 6 position being that for which the greatest latitude is offered.

Preferred compounds are those in which one or several of the substituents $R_1$, $R_4$ and $R_6$, independently of one another or simultaneously, are hydrogen.

Advantageous compounds are also those for which $R_4$ is the succinyl group $-CO-(CH_2)_2-CO_2H$ or the acetyl group.

Preferred compounds are also those for which $R_6$ is an acyl radical containing from 1 to 4 carbon atoms, and notably the acetyl ($-COCH_3$), succinyl($-CO(CH_2)_2-CO_2H$), radicals or again those for which $R_6$ is the mycoloyl group (about $C_{80}$ to $C_{90}$) or corynomycoloyl ($C_{32}$).

Preferred $R_2$ substituents are constituted by alkyl groups comprising from 1 to 4 carbon atoms and, in particularly preferred manner, $R_2$ is $-CH_3$.

Among the compounds according to the invention are particularly preferred those for which $R_1$, $R_4$, $R_6$ are simultaneously a hydrogen atom, R and $R_2$ are $-CH_3$, X is L-alanyl, Y is $-NH_2$ and $(A)_n$-Z is an esterified or amidified L-alanyl residue an esterified or amidified L-lysyl residue an ester residue.

In these groups $(A)_n$-Z, the ester or amide residues are preferably those of the hydrocarbon groups butyl, decyl, pentadecyl, eicosyl, benzyl, or a residue derived from an acid of the mycolic type such as glyceryl-mycolate.

Particularly preferred $(A)_n$-Z groups are those of the formulae $-NH-CH(CH_3)-COO-(CH_2)_{19}-CH_3$
$-NH-CH(CH_3)-CONH-(CH_2)_9-CH_3$
$-NH-CH(CH_3)-COO-(CH_2)_9-CH_3$
$-NH-CH(CH_3)-COO-(CH_2)_{14}-CH_3$
$-NH-CH(CH_3)-COO-(CH_2)_3-CH_3$
$-NH-CH(CH_3)-COO-CH_2-C_6H_5$
$-NH-CH(CH_3)-COO-CH_2-CHOH-CH_2-O-R°$, with R° corresponding to a micolic acid comprising from 80 to 90 carbons,
$-NH-CH[(CH_2)_4-NH_2]-COO-(CH_2)_9-CH_3$
$-O-(CH_2)_3-CH_3$
$-O-(CH_2)_9-CH_3$ Preferred compounds according to the invention are notably the following -N-acetyl-muramyl-L-alanyl-D-isoglutaminyl-L-alanyldecylamide of the formula

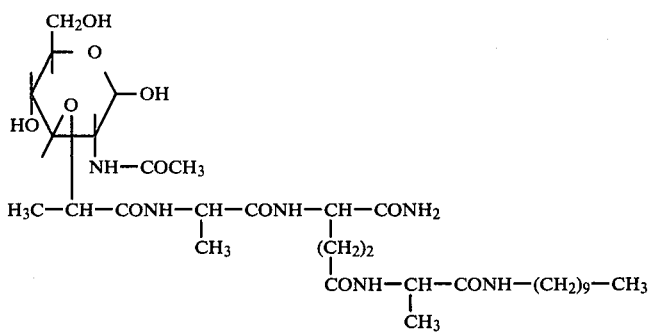

—N-acetyl-muramyl-L-alanyl-D-isoglutaminyl-decyl-ester of the formula

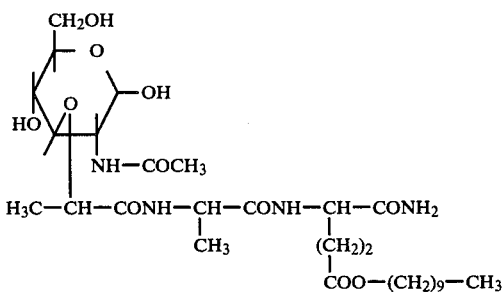

—β-D-p.-aminophenyl-N-acetyl-muramyl-L-alanyl-D-isoglutaminyl-L-alanyl-decyl-ester of the formula

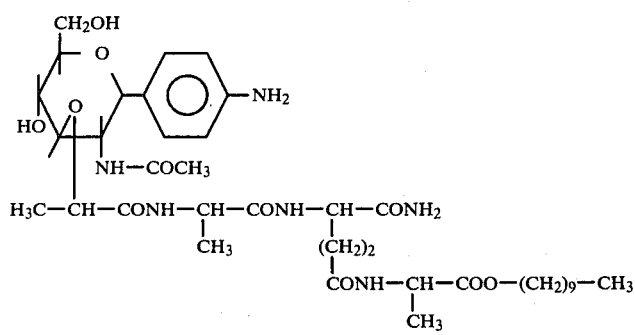

—N-acetyl-muramyl-L-alanyl-D-isoglutaminyl-L-alanylpentadecyl-ester of the formula

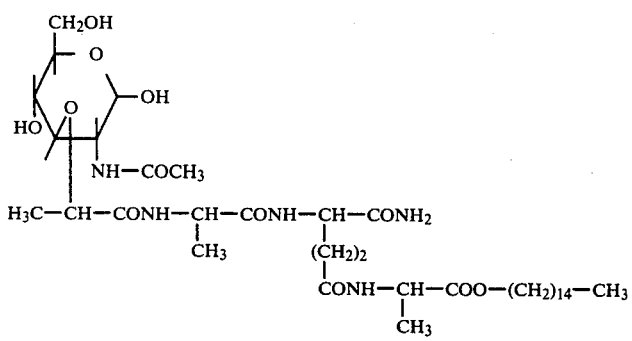

—N-acetyl-muramyl-L-alanyl-D-isoglutaminyl-L-alanyleicosyl-ester of the formula

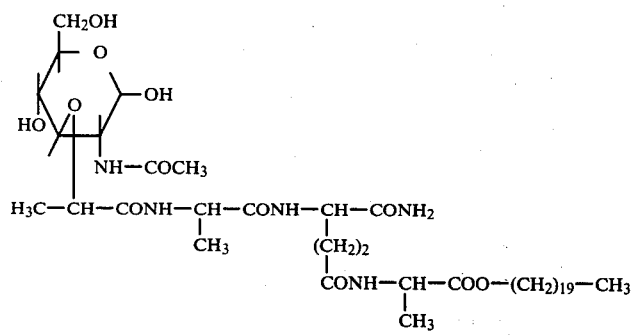

—N-acetyl-muramyl-L-alanyl-D-isoglutaminyl-L-alanylbenzyl-ester of the formula

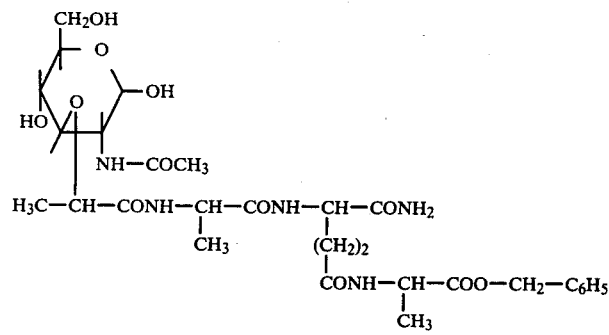

—N-acetyl-muramyl-L-alanyl-D-isoglutaminyl-L-alanyl-D-glyceryl-mycolate of the formula

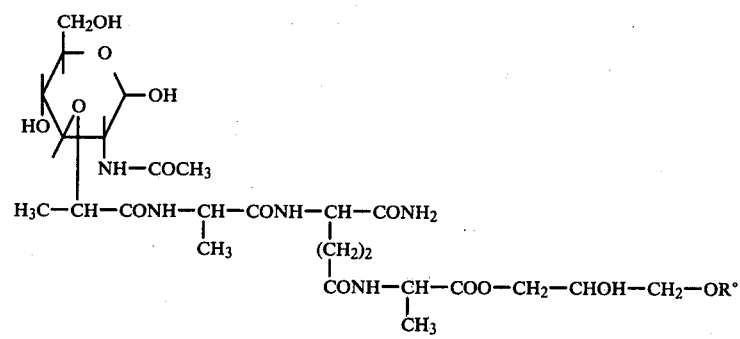

R° being a mycolic acid radical containing from 80 to 90 carbon atoms;

—N-acetyl-muramyl-L-alanyl-D-isoglutaminyl-L-lysinedecyl-ester of the formula

—N-acetyl-muramyl-L-alanyl-D-isoglutaminyl-butylester of the formula

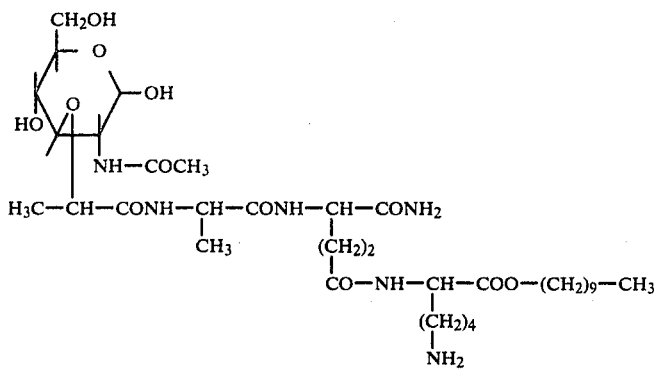

—N-acetyl-muramyl-L-alanyl-D-glutamyl-α-methyl-ester-γ-decyl-ester of the formula

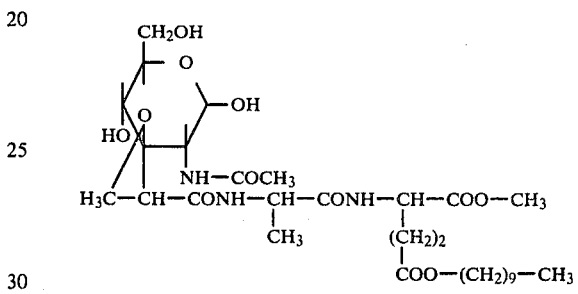

—N-acetyl-muramyl-L-alanyl-D-glutamyl-α-methyl-ester-γ-butyl-ester of the formula

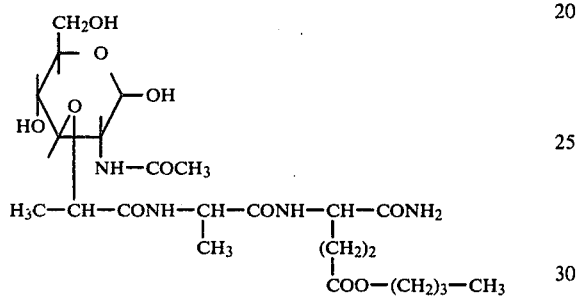

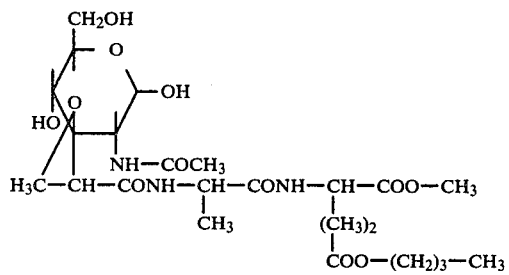

Other preferred compounds according to the invention are those corresponding to formula I in which the various substituents are those listed in the following table.

| $R_1$ | $R_2$ | $R_4$ | $R_6$ | R | X | Y | $-(A)_n-$ | Z |
|---|---|---|---|---|---|---|---|---|
| H | $CH_3$ | H | H | $CH_3$ | L-Ala | OH | n = 0 | $OC_5H_{11}$ |
| " | " | " | " | " | " | " | " | $OC_{10}H_{21}$ |
| " | " | " | " | " | " | " | " | $OC_{15}H_{31}$ |
| " | " | " | " | " | " | " | " | $OC_{20}H_{41}$ |
| " | " | " | " | " | " | " | " | $OC_7H_7$ |
| " | " | " | " | " | " | " | " | (1) |
| " | " | " | " | " | " | $NH_2$ | " | $OC_5H_{11}$ |
| " | " | " | " | " | " | " | " | $OC_{10}H_{21}$ |
| " | " | " | " | " | " | " | " | $OC_{15}H_{31}$ |
| " | " | " | " | " | " | " | " | $OC_{20}H_{41}$ |
| " | " | " | " | " | " | " | " | $OC_7H_7$ |
| " | " | " | " | " | " | " | " | (1) |
| " | " | " | " | " | " | $OCH_3$ | " | $OC_5H_{11}$ |
| " | " | " | " | " | " | " | " | $OC_{10}H_{21}$ |
| " | " | " | " | " | " | " | " | $OC_{15}H_{31}$ |
| " | " | " | " | " | " | " | " | $OC_{20}H_{41}$ |
| " | " | " | " | " | " | " | " | $OC_7H_7$ |
| " | " | " | " | " | " | " | " | (1) |
| " | " | " | " | " | " | $OC_4H_9$ | " | $OC_5H_{11}$ |
| " | " | " | " | " | " | " | " | $OC_{10}H_{21}$ |
| " | " | " | " | " | " | " | " | $OC_{15}H_{31}$ |
| " | " | " | " | " | " | " | " | $OC_{20}H_{41}$ |
| " | " | " | " | " | " | " | " | $OC_7H_7$ |

-continued

| R₁ | R₂ | R₄ | R₆ | R | X | Y | —(A)ₙ— | Z |
|---|---|---|---|---|---|---|---|---|
| " | " | " | " | " | " | " | " | (1) |
| " | " | " | " | " | " | NH—CH₃ | " | OC₅H₁₁ |
| " | " | " | " | " | " | " | " | OC₁₀H₂₁ |
| " | " | " | " | " | " | " | " | OC₁₅H₃₁ |
| " | " | " | " | " | " | " | " | OC₂₀H₄₁ |
| " | " | " | " | " | " | " | " | OC₇H₇ |
| " | " | " | " | " | " | " | " | (1) |
| " | " | " | " | " | " | NH—C₄H₉ | " | OC₅H₁₁ |
| " | " | " | " | " | " | " | " | OC₁₀H₂₁ |
| " | " | " | " | " | " | " | " | OC₁₅H₃₁ |
| " | " | " | " | " | " | " | " | OC₂₀H₄₁ |
| " | " | " | " | " | " | " | " | OC₇H₇ |
| " | " | " | " | " | " | " | " | (1) |
| " | " | " | " | " | " | OH | L-Ala | OC₅H₁₁ |
| " | " | " | " | " | " | " | " | OC₁₀H₂₁ |
| " | " | " | " | " | " | " | " | OC₁₅H₃₁ |
| " | " | " | " | " | " | " | " | OC₂₀H₄₁ |
| " | " | " | " | " | " | " | " | OC₇H₇ |
| " | " | " | " | " | " | " | " | (1) |
| " | " | " | " | " | " | " | " | (2) |
| " | " | " | " | " | " | " | " | (3) |
| " | " | " | " | " | " | " | " | NH—C₄H₉ |
| " | " | " | " | " | " | " | " | NH—C₂₀H₄₁ |
| " | " | " | " | " | " | NH₂ | " | OC₅H₁₁ |
| " | " | " | " | " | " | " | " | OC₁₀H₂₁ |
| " | " | " | " | " | " | " | " | OC₁₅H₃₁ |
| " | " | " | " | " | " | " | " | OC₂₀H₄₁ |
| " | " | " | " | " | " | " | " | OC₇H₇ |
| " | " | " | " | " | " | " | " | (1) |
| " | " | " | " | " | " | " | " | (2) |
| " | " | " | " | " | " | " | " | (3) |
| " | " | " | " | " | " | " | " | NH—C₄H₉ |
| " | " | " | " | " | " | " | " | NH—C₂₀H₄₁ |
| " | " | " | " | " | " | OCH₃ | " | OC₅H₁₁ |
| " | " | " | " | " | " | " | " | OC₁₅H₃₁ |
| " | " | " | " | " | " | " | " | OC₂₀H₄₁ |
| " | " | " | " | " | " | " | " | OC₇H₇ |
| " | " | " | " | " | " | " | " | (1) |
| " | " | " | " | " | " | " | " | (2) |
| " | " | " | " | " | " | " | " | (3) |
| " | " | " | " | " | " | " | " | NH—C₄H₉ |
| " | " | " | " | " | " | " | " | NH—C₂₀H₄₁ |
| " | " | " | " | " | " | OC₄H₉ | " | OC₅H₁₁ |
| " | " | " | " | " | " | " | " | OC₁₀H₂₁ |
| " | " | " | " | " | " | " | " | OC₁₅H₃₁ |
| " | " | " | " | " | " | " | " | OC₂₀H₄₁ |
| " | " | " | " | " | " | " | " | OC₇H₇ |
| " | " | " | " | " | " | " | " | (1) |
| " | " | " | " | " | " | " | " | (2) |
| " | " | " | " | " | " | " | " | (3) |
| " | " | " | " | " | " | " | " | NH—C₄H₉ |
| " | " | " | " | " | " | " | " | NH—C₂₀H₄₁ |
| " | " | " | " | " | " | NH—CH₃ | " | OC₅H₁₁ |
| " | " | " | " | " | " | " | " | OC₁₀H₂₁ |
| " | " | " | " | " | " | " | " | OC₁₅H₃₁ |
| " | " | " | " | " | " | " | " | OC₂₀H₄₁ |
| " | " | " | " | " | " | " | " | OC₇H₇ |
| " | " | " | " | " | " | " | " | (1) |
| " | " | " | " | " | " | " | " | (2) |
| " | " | " | " | " | " | " | " | (3) |
| " | " | " | " | " | " | " | " | NH—C₄H₉ |
| " | " | " | " | " | " | " | " | NH—C₂₀H₄₁ |
| " | " | " | " | " | " | NH—C₄H₉ | " | OC₅H₉ |
| " | " | " | " | " | " | " | " | OC₁₀H₂₁ |
| " | " | " | " | " | " | " | " | OC₁₅H₃₁ |
| " | " | " | " | " | " | " | " | OC₂₀H₄₁ |
| " | " | " | " | " | " | " | " | OC₇H₇ |
| " | " | " | " | " | " | " | " | (1) |
| " | " | " | " | " | " | " | " | (2) |
| " | " | " | " | " | " | " | " | (3) |
| " | " | " | " | " | " | " | " | NH—C₄H₉ |
| " | " | " | " | " | " | " | " | NH—C₂₀H₄₁ |
| " | " | " | " | " | " | OH | L-Lys | OC₅H₁₁ |
| " | " | " | " | " | " | " | " | OC₁₀H₂₁ |
| " | " | " | " | " | " | " | " | OC₁₅H₃₁ |
| " | " | " | " | " | " | " | " | OC₂₀H₄₁ |
| " | " | " | " | " | " | " | " | OC₇H₇ |
| " | " | " | " | " | " | " | " | (1) |
| " | " | " | " | " | " | " | " | (2) |
| " | " | " | " | " | " | " | " | (3) |
| " | " | " | " | " | " | " | " | NH—C₄H₉ |

-continued

| R₁ | R₂ | R₄ | R₆ | R | X | Y | —(A)ₙ— | Z |
|---|---|---|---|---|---|---|---|---|
| " | " | " | " | " | " | " | " | NH—C₂₀H₄₁ |
| " | " | " | " | " | " | NH₂ | " | OC₅H₁₁ |
| " | " | " | " | " | " | " | " | OC₁₀H₂₁ |
| " | " | " | " | " | " | " | " | OC₁₅H₃₁ |
| " | " | " | " | " | " | " | " | OC₂₀H₄₁ |
| " | " | " | " | " | " | " | " | OC₇H₇ |
| " | " | " | " | " | " | " | " | (1) |
| " | " | " | " | " | " | " | " | (2) |
| " | " | " | " | " | " | " | " | (3) |
| " | " | " | " | " | " | " | " | NH—C₄H₉ |
| " | " | " | " | " | " | " | " | NH—C₂₀H₄₁ |
| " | " | " | " | " | " | OCH₃ | " | OC₅H₁₁ |
| " | " | " | " | " | " | " | " | OC₁₅H₃₁ |
| " | " | " | " | " | " | " | " | OC₂₀H₄₁ |
| " | " | " | " | " | " | " | " | OC₇H₇ |
| " | " | " | " | " | " | " | " | (1) |
| " | " | " | " | " | " | " | " | (2) |
| " | " | " | " | " | " | " | " | (3) |
| " | " | " | " | " | " | " | " | NH—C₄H₉ |
| " | " | " | " | " | " | " | " | NH—C₂₀H₄₁ |
| " | " | " | " | " | " | OC₄H₉ | " | OC₅H₁₁ |
| " | " | " | " | " | " | " | " | OC₁₀H₂₁ |
| " | " | " | " | " | " | " | " | OC₁₅H₃₁ |
| " | " | " | " | " | " | " | " | OC₂₀H₄₁ |
| " | " | " | " | " | " | " | " | OC₇H₇ |
| " | " | " | " | " | " | " | " | (1) |
| " | " | " | " | " | " | " | " | (2) |
| " | " | " | " | " | " | " | " | NH—C₄H₉ |
| " | " | " | " | " | " | " | " | NH—C₂₀H₄₁ |
| " | " | " | " | " | " | NH—CH₃ | " | OC₅H₁₁ |
| " | " | " | " | " | " | " | " | OC₁₀H₂₁ |
| " | " | " | " | " | " | " | " | OC₁₅H₃₁ |
| " | " | " | " | " | " | " | " | OC₂₀H₄₁ |
| " | " | " | " | " | " | " | " | OC₇H₇ |
| " | " | " | " | " | " | " | " | (1) |
| " | " | " | " | " | " | " | " | (2) |
| " | " | " | " | " | " | " | " | (3) |
| " | " | " | " | " | " | " | " | NH—C₄H₉ |
| " | " | " | " | " | " | " | " | NH—C₂₀H₄₁ |
| " | " | " | " | " | " | NH—C₄H₉ | " | OC₅H₁₁ |
| " | " | " | " | " | " | " | " | OC₁₀H₂₁ |
| " | " | " | " | " | " | " | " | OC₁₅H₃₁ |
| " | " | " | " | " | " | " | " | OC₂₀H₄₁ |
| " | " | " | " | " | " | " | " | OC₇H₇ |
| " | " | " | " | " | " | " | " | (1) |
| " | " | " | " | " | " | " | " | (2) |
| " | " | " | " | " | " | " | " | (3) |
| " | " | " | " | " | " | " | " | NH—C₄H₉ |
| " | " | " | " | " | " | " | " | NH—C₂₀H₄₁ |
| " | " | " | " | " | " | OH | L-Glu | PC₅H₁₁ |
| " | " | " | " | " | " | " | " | OC₁₀H₂₁ |
| " | " | " | " | " | " | " | " | OC₁₅H₃₁ |
| " | " | " | " | " | " | " | " | OC₂₀H₄₁ |
| " | " | " | " | " | " | " | " | OC₇H₇ |
| " | " | " | " | " | " | " | " | (1) |
| " | " | " | " | " | " | " | " | (2) |
| " | " | " | " | " | " | " | " | (2) |
| " | " | " | " | " | " | " | " | (3) |
| " | " | " | " | " | " | " | " | NH—C₄H₉ |
| " | " | " | " | " | " | " | " | NH—C₂₀H₄₁ |
| " | " | " | " | " | " | NH₂ | " | OC₅H₁₁ |
| " | " | " | " | " | " | " | " | OC₁₀H₂₁ |
| " | " | " | " | " | " | " | " | OC₁₅H₃₁ |
| " | " | " | " | " | " | " | " | OC₂₀H₄₁ |
| " | " | " | " | " | " | " | " | OC₇H₇ |
| " | " | " | " | " | " | " | " | (1) |
| " | " | " | " | " | " | " | " | (2) |
| " | " | " | " | " | " | " | " | (3) |
| " | " | " | " | " | " | " | " | NH—C₄H₉ |
| " | " | " | " | " | " | " | " | NH—C₂₀H₄₁ |
| " | " | " | " | " | " | OCH₃ | " | OC₅H₁₁ |
| " | " | " | " | " | " | " | " | OC₁₀H₂₁ |
| " | " | " | " | " | " | " | " | OC₁₅H₃₁ |
| " | " | " | " | " | " | " | " | OC₂₀H₄₁ |
| " | " | " | " | " | " | " | " | OC₇H₇ |
| " | " | " | " | " | " | " | " | (1) |
| " | " | " | " | " | " | " | " | (2) |
| " | " | " | " | " | " | " | " | (3) |
| " | " | " | " | " | " | " | " | NH—C₄H₉ |
| " | " | " | " | " | " | " | " | NH—C₂₀H₄₁ |
| " | " | " | " | " | " | OC₄H₉ | " | OC₅H₁₁ |

-continued

| R₁ | R₂ | R₄ | R₆ | R | X | Y | —(A)ₙ— | Z |
|---|---|---|---|---|---|---|---|---|
| " | " | " | " | " | " | " | " | OC₁₀H₂₁ |
| " | " | " | " | " | " | " | " | OC₁₅H₃₁ |
| " | " | " | " | " | " | " | " | OC₂₀H₄₁ |
| " | " | " | " | " | " | " | " | OC₇H₇ |
| " | " | " | " | " | " | " | " | (1) |
| " | " | " | " | " | " | " | " | (2) |
| " | " | " | " | " | " | " | " | (3) |
| " | " | " | " | " | " | " | " | NH—C₄H₉ |
| " | " | " | " | " | " | " | " | NH—C₂₀H₄₁ |
| " | " | " | " | " | " | NH—CH₃ | " | OC₅H₁₁ |
| " | " | " | " | " | " | " | " | OC₁₀H₂₁ |
| " | " | " | " | " | " | " | " | OC₁₅H₃₁ |
| " | " | " | " | " | " | " | " | OC₂₀H₄₁ |
| " | " | " | " | " | " | " | " | OC₇H₇ |
| " | " | " | " | " | " | " | " | (1) |
| " | " | " | " | " | " | " | " | (2) |
| " | " | " | " | " | " | " | " | (3) |
| " | " | " | " | " | " | " | " | NH—C₄H₉ |
| " | " | " | " | " | " | " | " | NH—C₂₀H₄₁ |
| " | " | " | " | " | " | NH—C₄H₉ | " | OC₅H₁₁ |
| " | " | " | " | " | " | " | " | OC₁₀H₂₁ |
| " | " | " | " | " | " | " | " | OC₁₅H₃₁ |
| " | " | " | " | " | " | " | " | OC₂₀H₄₁ |
| " | " | " | " | " | " | " | " | OC₇H₇ |
| " | " | " | " | " | " | " | " | (1) |
| " | " | " | " | " | " | " | " | (2) |
| " | " | " | " | " | " | " | " | (3) |
| " | " | " | " | " | " | " | " | NH—C₄H₉ |
| " | " | " | " | " | " | " | " | NH—C₂₀H₄₁ |
| " | " | " | " | " | Gly | OH | n = 0 | OC₁₀H₂₁ |
| " | " | " | " | " | " | " | " | OC₂₀H₄₁ |
| " | " | " | " | " | " | " | " | (1) |
| " | " | " | " | " | " | NH₂ | " | OC₁₀H₂₁ |
| " | " | " | " | " | " | " | " | OC₂₀H₄₁ |
| " | " | " | " | " | " | " | " | (1) |
| " | " | " | " | " | " | OCH₃ | " | OC₁₀H₂₁ |
| " | " | " | " | " | " | " | " | OC₂₀H₄₁ |
| " | " | " | " | " | " | " | " | (1) |
| " | " | " | " | " | " | OC₄H₉ | " | OC₁₀H₂₁ |
| " | " | " | " | " | " | " | " | OC₂₀H₄₁ |
| " | " | " | " | " | " | " | " | (1) |
| " | " | " | " | " | " | NH—CH₃ | " | OC₁₀H₂₁ |
| " | " | " | " | " | " | " | " | OC₂₀H₄₁ |
| " | " | " | " | " | " | " | " | (1) |
| " | " | " | " | " | " | NH—C₄H₉ | " | OC₁₀H₂₁ |
| " | " | " | " | " | " | " | " | OC₂₀H₄₁ |
| " | " | " | " | " | " | " | " | (1) |
| " | " | " | " | " | " | OH | Ala | OC₁₀H₂₁ |
| " | " | " | " | " | " | " | " | OC₂₀H₄₁ |
| " | " | " | " | " | " | " | " | (1) |
| " | " | " | " | " | " | " | " | (3) |
| " | " | " | " | " | " | " | " | NH—C₂₀H₄₁ |
| " | " | " | " | " | " | NH₂ | " | OC₁₀H₂₁ |
| " | " | " | " | " | " | " | " | OC₂₀H₄₁ |
| " | " | " | " | " | " | " | " | (1) |
| " | " | " | " | " | " | " | " | (3) |
| " | " | " | " | " | " | " | " | NH—C₂₀H₄₁ |
| " | " | " | " | " | " | OC₄H₉ | " | OC₁₀H₂₁ |
| " | " | " | " | " | " | " | " | OC₂₀H₄₁ |
| " | " | " | " | " | " | " | " | (1) |
| " | " | " | " | " | " | " | " | (3) |
| " | " | " | " | " | " | " | " | NH—C₂₀H₄₁ |
| " | " | " | " | " | " | NH—C₄H₉ | " | OC₁₀H₂₁ |
| " | " | " | " | " | " | " | " | OC₂₀H₄₁ |
| " | " | " | " | " | " | " | " | (1) |
| " | " | " | " | " | " | " | " | (3) |
| " | " | " | " | " | " | " | " | NH—C₂₀H₄₁ |
| " | " | " | " | " | Ser | OH | n = 0 | OC₁₀H₂₁ |
| " | " | " | " | " | " | " | " | OC₂₀H₄₁ |
| " | " | " | " | " | " | " | " | (1) |
| " | " | " | " | " | " | NH₂ | " | OC₁₀H₂₁ |
| " | " | " | " | " | " | " | " | OC₂₀H₄₁ |
| " | " | " | " | " | " | " | " | (1) |
| " | " | " | " | " | " | OCH₃ | " | OC₁₀H₂₁ |
| " | " | " | " | " | " | " | " | OC₂₀H₄₁ |
| " | " | " | " | " | " | " | " | (1) |
| " | " | " | " | " | " | OC₄H₉ | " | OC₁₀H₂₁ |
| " | " | " | " | " | " | " | " | OC₂₀H₄₁ |
| " | " | " | " | " | " | " | " | (1) |
| " | " | " | " | " | " | NH—CH₃ | " | OC₁₀H₂₁ |
| " | " | " | " | " | " | " | " | OC₂₀H₄₁ |

-continued

| R₁ | R₂ | R₄ | R₆ | R | X | Y | —(A)ₙ— | Z |
|---|---|---|---|---|---|---|---|---|
| ″ | ″ | ″ | ″ | ″ | ″ | ″ | ″ | (1) |
| ″ | ″ | ″ | ″ | ″ | ″ | NH—C₄H₉ | ″ | OC₁₀H₂₁ |
| ″ | ″ | ″ | ″ | ″ | ″ | ″ | ″ | OC₂₀H₄₁ |
| ″ | ″ | ″ | ″ | ″ | ″ | ″ | ″ | (1) |
| ″ | ″ | ″ | ″ | ″ | ″ | OH | Ala | OC₁₀H₂₁ |
| ″ | ″ | ″ | ″ | ″ | ″ | ″ | ″ | OC₂₀H₄₁ |
| ″ | ″ | ″ | ″ | ″ | ″ | ″ | ″ | (1) |
| ″ | ″ | ″ | ″ | ″ | ″ | ″ | ″ | (3) |
| ″ | ″ | ″ | ″ | ″ | ″ | ″ | ″ | NH—C₂₀H₄₁ |
| ″ | ″ | ″ | ″ | ″ | ″ | NH₂ | ″ | OC₁₀H₂₁ |
| ″ | ″ | ″ | ″ | ″ | ″ | ″ | ″ | OC₂₀H₄₁ |
| ″ | ″ | ″ | ″ | ″ | ″ | ″ | ″ | (1) |
| ″ | ″ | ″ | ″ | ″ | ″ | ″ | ″ | (3) |
| ″ | ″ | ″ | ″ | ″ | ″ | ″ | ″ | NH—C₂₀H₄₁ |
| ″ | ″ | ″ | ″ | ″ | ″ | OC₄H₉ | ″ | OC₁₀H₂₁ |
| ″ | ″ | ″ | ″ | ″ | ″ | ″ | ″ | OC₂₀H₄₁ |
| ″ | ″ | ″ | ″ | ″ | ″ | ″ | ″ | (1) |
| ″ | ″ | ″ | ″ | ″ | ″ | ″ | ″ | (3) |
| ″ | ″ | ″ | ″ | ″ | ″ | ″ | ″ | NH—C₂₀H₄₁ |
| ″ | ″ | ″ | ″ | ″ | ″ | NH—C₄H₉ | ″ | OC₁₀H₂₁ |
| ″ | ″ | ″ | ″ | ″ | ″ | ″ | ″ | OC₂₀H₄₁ |
| ″ | ″ | ″ | ″ | ″ | ″ | ″ | ″ | (1) |
| ″ | ″ | ″ | ″ | ″ | ″ | ″ | ″ | (3) |
| ″ | ″ | ″ | ″ | ″ | ″ | ″ | ″ | NH—C₂₀H₄₁ |
| ″ | ″ | ″ | ″ | ″ | Val | OH | n = 0 | OC₁₀H₂₁ |
| ″ | ″ | ″ | ″ | ″ | ″ | ″ | ″ | OC₂₀H₄₁ |
| ″ | ″ | ″ | ″ | ″ | ″ | ″ | ″ | (1) |
| ″ | ″ | ″ | ″ | ″ | ″ | NH₂ | ″ | OC₁₀H₂₁ |
| ″ | ″ | ″ | ″ | ″ | ″ | ″ | ″ | OC₂₀H₄₁ |
| ″ | ″ | ″ | ″ | ″ | ″ | ″ | ″ | (1) |
| ″ | ″ | ″ | ″ | ″ | ″ | OCH₃ | ″ | OC₁₀H₂₁ |
| ″ | ″ | ″ | ″ | ″ | ″ | ″ | ″ | OC₂₀H₄₁ |
| ″ | ″ | ″ | ″ | ″ | ″ | ″ | ″ | (1) |
| ″ | ″ | ″ | ″ | ″ | ″ | OC₄H₉ | ″ | OC₁₀H₂₁ |
| ″ | ″ | ″ | ″ | ″ | ″ | ″ | ″ | OC₂₀H₄₁ |
| ″ | ″ | ″ | ″ | ″ | ″ | ″ | ″ | (1) |
| ″ | ″ | ″ | ″ | ″ | ″ | NH—CH₃ | ″ | OC₁₀H₂₁ |
| ″ | ″ | ″ | ″ | ″ | ″ | ″ | ″ | OC₂₀H₄₁ |
| ″ | ″ | ″ | ″ | ″ | ″ | ″ | ″ | (1) |
| ″ | ″ | ″ | ″ | ″ | ″ | NH—C₄H₉ | ″ | OC₁₀H₂₁ |
| ″ | ″ | ″ | ″ | ″ | ″ | ″ | ″ | OC₂₀H₄₁ |
| ″ | ″ | ″ | ″ | ″ | ″ | ″ | ″ | (1) |
| ″ | ″ | ″ | ″ | ″ | ″ | OH | Ala | OC₁₀H₂₁ |
| ″ | ″ | ″ | ″ | ″ | ″ | ″ | ″ | OC₂₀H₄₁ |
| ″ | ″ | ″ | ″ | ″ | ″ | ″ | ″ | (1) |
| ″ | ″ | ″ | ″ | ″ | ″ | ″ | ″ | (3) |
| ″ | ″ | ″ | ″ | ″ | ″ | NH₂ | ″ | OC₁₀H₂₁ |
| ″ | ″ | ″ | ″ | ″ | ″ | ″ | ″ | OC₂₀H₄₁ |
| ″ | ″ | ″ | ″ | ″ | ″ | ″ | ″ | (1) |
| ″ | ″ | ″ | ″ | ″ | ″ | ″ | ″ | (3) |
| ″ | ″ | ″ | ″ | ″ | ″ | ″ | ″ | NH—C₂₀H₄₁ |
| ″ | ″ | ″ | ″ | ″ | ″ | OC₄H₉ | ″ | OC₁₀H₂₁ |
| ″ | ″ | ″ | ″ | ″ | ″ | ″ | ″ | OC₂₀H₄₁ |
| ″ | ″ | ″ | ″ | ″ | ″ | ″ | ″ | (1) |
| ″ | ″ | ″ | ″ | ″ | ″ | ″ | ″ | (3) |
| ″ | ″ | ″ | ″ | ″ | ″ | ″ | ″ | NH—C₂₀H₄₁ |
| ″ | ″ | ″ | ″ | ″ | ″ | NH—C₄H₉ | ″ | OC₁₀H₂₁ |
| ″ | ″ | ″ | ″ | ″ | ″ | ″ | ″ | OC₂₀H₄₁ |
| ″ | ″ | ″ | ″ | ″ | ″ | ″ | ″ | (1) |
| ″ | ″ | ″ | ″ | ″ | ″ | ″ | ″ | (3) |
| ″ | ″ | ″ | ″ | ″ | ″ | ″ | ″ | NH—C₂₀H₄₁ |
| ″ | ″ | ″ | ″ | H | L-Ala | OH | n = 0 | OC₁₀H₂₁ |
| ″ | ″ | ″ | ″ | ″ | ″ | ″ | ″ | OC₂₀H₄₁ |
| ″ | ″ | ″ | ″ | ″ | ″ | ″ | ″ | (1) |
| ″ | ″ | ″ | ″ | ″ | ″ | NH₂ | ″ | OC₁₀H₂₁ |
| ″ | ″ | ″ | ″ | ″ | ″ | ″ | ″ | OC₂₀H₄₁ |
| ″ | ″ | ″ | ″ | ″ | ″ | ″ | ″ | (1) |
| ″ | ″ | ″ | ″ | ″ | ″ | OC₄H₉ | ″ | OC₁₀H₂₁ |
| ″ | ″ | ″ | ″ | ″ | ″ | ″ | ″ | OC₂₀H₄₁ |
| ″ | ″ | ″ | ″ | ″ | ″ | ″ | ″ | (1) |
| ″ | ″ | ″ | ″ | ″ | ″ | NH—C₄H₉ | ″ | OC₁₀H₂₁ |
| ″ | ″ | ″ | ″ | ″ | ″ | ″ | ″ | OC₂₀H₄₁ |
| ″ | ″ | ″ | ″ | ″ | ″ | ″ | ″ | (1) |
| ″ | ″ | ″ | ″ | ″ | ″ | OH | Ala | OC₁₀H₂₁ |
| ″ | ″ | ″ | ″ | ″ | ″ | ″ | ″ | OC₂₀H₄₁ |
| ″ | ″ | ″ | ″ | ″ | ″ | ″ | ″ | (1) |
| ″ | ″ | ″ | ″ | ″ | ″ | ″ | ″ | (3) |
| ″ | ″ | ″ | ″ | ″ | ″ | ″ | NH₂ | OC₁₀H₂₁ |
| ″ | ″ | ″ | ″ | ″ | ″ | ″ | ″ | OC₂₀H₄₁ |
| ″ | ″ | ″ | ″ | ″ | ″ | ″ | ″ | (1) |
| ″ | ″ | ″ | ″ | ″ | ″ | ″ | ″ | (3) |

-continued

| R₁ | R₂ | R₄ | R₆ | R | X | Y | —(A)ₙ— | Z |
|---|---|---|---|---|---|---|---|---|
| "  | "  | "  | "  | "  | "  | "        | "     | NH—C₂₀H₄₁ |
| "  | "  | "  | "  | "  | "  | OC₄H₉    | "     | OC₁₀H₂₁ |
| "  | "  | "  | "  | "  | "  | "        | "     | OC₂₀H₄₁ |
| "  | "  | "  | "  | H  | "  | "        | "     | (1) |
| "  | "  | "  | "  | "  | "  | "        | "     | (3) |
| "  | "  | "  | "  | "  | "  | "        | "     | NH—C₂₀H₄₁ |
| "  | "  | "  | "  | "  | "  | NH—C₄H₉  | "     | OC₁₀H₂₁ |
| "  | "  | "  | "  | "  | "  | "        | "     | OC₂₀H₄₁ |
| "  | "  | "  | "  | "  | "  | "        | "     | (1) |
| "  | "  | "  | "  | "  | "  | "        | "     | (3) |
| "  | "  | "  | "  | "  | "  | "        | "     | NH—C₂₀H₄₁ |
| "  | "  | "  | "  | "  | "  | OH       | Lys   | OC₁₀H₂₁ |
| "  | "  | "  | "  | "  | "  | "        | "     | OC₂₀H₄₁ |
| "  | "  | "  | "  | "  | "  | "        | "     | (1) |
| "  | "  | "  | "  | "  | "  | "        | "     | (3) |
| "  | "  | "  | "  | "  | "  | NH₂      | "     | NH—C₂₀H₄₁ |
| "  | "  | "  | "  | "  | "  | "        | "     | OC₁₀H₂₁ |
| "  | "  | "  | "  | "  | "  | "        | "     | OC₂₀H₄₁ |
| "  | "  | "  | "  | "  | "  | "        | "     | (1) |
| "  | "  | "  | "  | "  | "  | "        | "     | (3) |
| "  | "  | "  | "  | "  | "  | OC₄H₉    | "     | OC₁₀H₂₁ |
| "  | "  | "  | "  | "  | "  | "        | "     | OC₂₀H₄₁ |
| "  | "  | "  | "  | "  | "  | "        | "     | (1) |
| "  | "  | "  | "  | "  | "  | "        | "     | (3) |
| "  | "  | "  | "  | "  | "  | "        | "     | NH—C₂₀H₄₁ |
| "  | "  | "  | "  | "  | "  | NH—C₄H₉  | "     | OC₁₀H₂₁ |
| "  | "  | "  | "  | "  | "  | "        | "     | OC₂₀H₄₁ |
| "  | "  | "  | "  | "  | "  | "        | "     | (1) |
| "  | "  | "  | "  | "  | "  | "        | "     | (3) |
| "  | "  | "  | "  | "  | "  | "        | "     | NH—C₂₀H₄₁ |
| "  | "  | "  | "  | "  | "  | OH       | Glu   | OC₁₀H₂₁ |
| "  | "  | "  | "  | "  | "  | "        | "     | OC₂₀H₄₁ |
| "  | "  | "  | "  | "  | "  | "        | "     | (1) |
| "  | "  | "  | "  | "  | "  | "        | "     | (3) |
| "  | "  | "  | "  | "  | "  | "        | "     | NH—C₂₀H₄₁ |
| "  | "  | "  | "  | "  | "  | NH₂      | "     | OC₁₀H₂₁ |
| "  | "  | "  | "  | "  | "  | "        | "     | OC₂₀H₄₁ |
| "  | "  | "  | "  | "  | "  | "        | "     | (1) |
| "  | "  | "  | "  | "  | "  | "        | "     | (3) |
| "  | "  | "  | "  | "  | "  | "        | "     | NH—C₂₀H₄₁ |
| "  | "  | "  | "  | "  | "  | OC₄H₉    | "     | OC₁₀H₂₁ |
| "  | "  | "  | "  | "  | "  | "        | "     | OC₂₀H₄₁ |
| "  | "  | "  | "  | "  | "  | "        | "     | (1) |
| "  | "  | "  | "  | "  | "  | "        | "     | (3) |
| "  | "  | "  | "  | "  | "  | "        | "     | NH—C₂₀H₄₁ |
| "  | "  | "  | "  | "  | "  | NH—C₄H₉  | "     | OC₁₀H₂₁ |
| "  | "  | "  | "  | "  | "  | "        | "     | OC₂₀H₄₁ |
| "  | "  | "  | "  | "  | "  | "        | "     | (1) |
| "  | "  | "  | "  | "  | "  | "        | "     | (3) |
| "  | "  | "  | "  | "  | "  | "        | "     | NH—C₂₀H₄₁ |
| "  | "  | "  | "  | "  | Gly | OH      | n = 0 | OC₁₀H₂₁ |
| "  | "  | "  | "  | "  | "  | "        | "     | OC₂₀H₄₁ |
| "  | "  | "  | "  | "  | "  | "        | "     | (1) |
| "  | "  | "  | "  | "  | "  | NH₂      | "     | OC₁₀H₂₁ |
| "  | "  | "  | "  | "  | "  | "        | "     | OC₂₀H₄₁ |
| "  | "  | "  | "  | "  | "  | "        | "     | (1) |
| "  | "  | "  | "  | "  | "  | OC₄H₉    | "     | OC₁₀H₂₁ |
| "  | "  | "  | "  | "  | "  | "        | "     | OC₂₀H₄₁ |
| "  | "  | "  | "  | "  | "  | "        | "     | (1) |
| "  | "  | "  | "  | "  | "  | NH—C₄H₉  | "     | OC₁₀H₂₁ |
| "  | "  | "  | "  | "  | "  | "        | "     | OC₂₀H₄₁ |
| "  | "  | "  | "  | "  | "  | "        | "     | (1) |
| "  | "  | "  | "  | "  | "  | OH       | Ala   | OC₁₀H₂₁ |
| "  | "  | "  | "  | "  | "  | "        | "     | OC₂₀H₄₁ |
| "  | "  | "  | "  | "  | "  | "        | "     | (1) |
| "  | "  | "  | "  | "  | "  | "        | "     | (3) |
| "  | "  | "  | "  | "  | "  | "        | "     | NH—C₂₀H₄₁ |
| "  | "  | "  | "  | "  | "  | NH₂      | "     | OC₁₀H₂₁ |
| "  | "  | "  | "  | "  | "  | "        | "     | OC₂₀H₄₁ |
| "  | "  | "  | "  | "  | "  | "        | "     | (1) |
| "  | "  | "  | "  | "  | "  | "        | "     | (3) |
| "  | "  | "  | "  | "  | "  | "        | "     | NH—C₂₀H₄₁ |
| "  | "  | "  | "  | "  | "  | OC₄H₉    | "     | OC₁₀H₂₁ |
| "  | "  | "  | "  | "  | "  | "        | "     | OC₂₀H₄₁ |
| "  | "  | "  | "  | "  | "  | "        | "     | (1) |
| "  | "  | "  | "  | "  | "  | "        | "     | (3) |
| "  | "  | "  | "  | "  | "  | "        | "     | NH—C₂₀H₄₁ |
| "  | "  | "  | "  | "  | "  | NH—C₄H₉  | "     | OC₁₀H₂₁ |
| "  | "  | "  | "  | "  | "  | "        | "     | OC₂₀H₄₁ |
| "  | "  | "  | "  | "  | "  | "        | "     | (1) |

-continued

| $R_1$ | $R_2$ | $R_4$ | $R_6$ | R | X | Y | $-(A)_n-$ | Z |
|---|---|---|---|---|---|---|---|---|
| " | " | " | " | " | " | " | " | (3) |
| " | " | " | " | " | " | " | " | $NH-C_{20}H_{41}$ |
| " | " | " | " | " | L-Ser | OH | n = 0 | $OC_{10}H_{21}$ |
| " | " | " | " | " | " | " | " | $OC_{20}H_{41}$ |
| " | " | " | " | " | " | " | " | (1) |
| " | " | " | " | " | " | $NH_2$ | " | $OC_{10}H_{21}$ |
| " | " | " | " | " | " | " | " | $OC_{20}H_{41}$ |
| " | " | " | " | " | " | " | " | (1) |
| " | " | " | " | " | " | $OC_4H_9$ | " | $OC_{10}H_{21}$ |
| " | " | " | " | " | " | " | " | $OC_{20}H_{41}$ |
| " | " | " | " | " | " | " | " | (1) |
| " | " | " | " | " | " | $NH-C_4H_9$ | " | $OC_{10}H_{21}$ |
| " | " | " | " | " | " | " | " | $OC_{20}H_{41}$ |
| " | " | " | " | " | " | " | " | (1) |
| " | " | " | " | " | " | OH | Ala | $OC_{10}H_{21}$ |
| " | " | " | " | " | " | " | " | $OC_{20}H_{41}$ |
| " | " | " | " | " | " | " | " | (1) |
| " | " | " | " | " | " | " | " | (3) |
| " | " | " | " | " | " | " | " | $NH-C_{20}H_{41}$ |
| " | " | " | " | " | " | $NH_2$ | " | $OC_{10}H_{21}$ |
| " | " | " | " | " | " | " | " | $OC_{20}H_{41}$ |
| " | " | " | " | " | " | " | " | (1) |
| " | " | " | " | " | " | " | " | (3) |
| " | " | " | " | " | " | " | " | $NH-C_{20}H_{41}$ |
| " | " | " | " | " | " | $OC_4H_9$ | " | $OC_{10}H_{21}$ |
| " | " | " | " | " | " | " | " | $OC_{20}H_{41}$ |
| " | " | " | " | " | " | " | " | (1) |
| " | " | " | " | " | " | " | " | (3) |
| " | " | " | " | " | " | " | " | $NH-C_{20}H_{41}$ |
| " | " | " | " | " | " | $NH-C_4H_9$ | " | $OC_{10}H_{21}$ |
| " | " | " | " | " | " | " | " | $OC_{20}H_{41}$ |
| " | " | " | " | " | " | " | " | (1) |
| " | " | " | " | " | " | " | " | (3) |
| " | " | " | " | " | " | " | " | $NH-C_{20}H_{41}$ |
| " | " | " | " | " | L-Val | OH | n = 0 | $OC_{10}H_{21}$ |
| " | " | " | " | " | " | " | " | $OC_{20}H_{41}$ |
| " | " | " | " | " | " | " | " | (1) |
| " | " | " | " | " | " | $NH_2$ | " | $OC_{10}H_{21}$ |
| " | " | " | " | " | " | " | " | $OC_{20}H_{41}$ |
| " | " | " | " | " | " | " | " | (1) |
| " | " | " | " | " | " | $OC_4H_9$ | " | $OC_{10}H_{21}$ |
| " | " | " | " | " | " | " | " | $OC_{20}H_{41}$ |
| " | " | " | " | " | " | " | " | (1) |
| " | " | " | " | " | " | $NH-C_4H_9$ | " | $OC_{10}H_{21}$ |
| " | " | " | " | " | " | " | " | $OC_{20}H_{41}$ |
| " | " | " | " | " | " | " | " | (1) |
| " | " | " | " | " | " | OH | Ala | $OC_{10}H_{21}$ |
| " | " | " | " | " | " | " | " | $OC_{20}H_{41}$ |
| " | " | " | " | " | " | " | " | (1) |
| " | " | " | " | " | " | " | " | (3) |
| " | " | " | " | " | " | " | " | $NH-C_{20}H_{41}$ |
| " | " | " | " | " | " | $NH_2$ | " | $OC_{10}H_{21}$ |
| " | " | " | " | " | " | " | " | $OC_{20}H_{41}$ |
| " | " | " | " | " | " | " | " | (1) |
| " | " | " | " | " | " | " | " | (3) |
| " | " | " | " | " | " | " | " | $NH-C_{20}H_{41}$ |
| " | " | " | " | " | " | $OC_4H_9$ | " | $OC_{10}H_{21}$ |
| " | " | " | " | " | " | " | " | $OC_{20}H_{41}$ |
| " | " | " | " | " | " | " | " | (1) |
| " | " | " | " | " | " | " | " | (3) |
| " | " | " | " | " | " | " | " | $NH-C_{20}H_{41}$ |
| " | " | " | " | " | " | $NH-C_4H_9$ | " | $OC_{10}H_{21}$ |
| " | " | " | " | " | " | " | " | $OC_{20}H_{41}$ |
| " | " | " | " | " | " | " | " | (1) |
| " | " | " | " | " | " | " | " | (3) |
| " | " | " | " | " | " | " | " | $NH-C_{20}H_{41}$ |
| " | " | " | " | $C_2H_5$ | L-Ala | $NH_2$ | n = 0 | $OC_{10}H_{21}$ |
| " | " | " | " | " | " | " | " | $OC_{20}H_{41}$ |
| " | " | " | " | " | " | " | " | (1) |
| " | " | " | " | " | " | $OC_4H_9$ | " | $OC_{10}H_{21}$ |
| " | " | " | " | " | " | " | " | $OC_{20}H_{41}$ |
| " | " | " | " | " | " | " | " | (1) |
| " | " | " | " | " | " | $NH_2$ | L-Ala | $OC_{10}H_{21}$ |
| " | " | " | " | " | " | " | " | $OC_{20}H_{41}$ |
| " | " | " | " | " | " | " | " | (1) |
| " | " | " | " | " | " | " | " | (3) |
| " | " | " | " | " | " | " | " | $NH-C_{20}H_{41}$ |
| " | " | " | " | " | " | $OC_4H_9$ | " | $OC_{10}H_{21}$ |
| " | " | " | " | " | " | " | " | $OC_{20}H_{41}$ |
| " | " | " | " | " | " | " | " | (1) |
| " | " | " | " | " | " | " | " | (3) |

-continued

| $R_1$ | $R_2$ | $R_4$ | $R_6$ | R | X | Y | $-(A)_n-$ | Z |
|---|---|---|---|---|---|---|---|---|
| " | " | " | " | " | " | " | " | $NH-C_{20}H_{41}$ |
| " | " | " | " | $CH_3$ | " | $NH_2$ | n = 0 | $OC_{10}H_{21}$ |
| " | " | " | " | " | " | " | " | $OC_{20}H_{41}$ |
| " | " | " | " | " | " | " | " | (1) |
| " | " | " | " | " | " | $OC_4H_9$ | " | $OC_{10}H_{21}$ |
| " | " | " | " | " | " | " | " | $OC_{20}H_{41}$ |
| " | " | " | " | " | " | " | " | (1) |
| " | " | " | " | " | " | $NH_2$ | L-Ala | $OC_{10}H_{21}$ |
| " | " | " | " | " | " | " | " | $OC_{20}H_{41}$ |
| " | " | " | " | " | " | " | " | (1) |
| " | " | " | " | " | " | " | " | (3) |
| " | " | " | " | " | " | " | " | $NH-C_{20}H_{41}$ |
| " | " | " | " | " | " | $OC_4H_9$ | " | $OC_{10}H_{21}$ |
| " | " | " | " | " | " | " | " | (1) |
| " | " | " | " | " | " | " | " | (3) |
| " | " | " | " | " | " | " | " | $NH-C_{20}H_{41}$ |
| " | " | " | " | H | " | $NH_2$ | n = 0 | $OC_{10}H_{21}$ |
| " | " | " | " | " | " | " | " | $OC_{20}H_{41}$ |
| " | " | " | " | " | " | " | " | (1) |
| " | " | " | " | " | " | $OC_4H_9$ | " | $OC_{10}H_{21}$ |
| " | " | " | " | " | " | " | " | $OC_{20}H_{41}$ |
| " | " | " | " | " | " | " | " | (1) |
| " | " | " | " | " | " | $NH_2$ | L-Ala | $OC_{10}H_{21}$ |
| " | " | " | " | " | " | " | " | $OC_{20}H_{41}$ |
| " | " | " | " | " | " | " | " | (1) |
| " | " | " | " | " | " | " | " | (3) |
| " | " | " | " | " | " | " | " | $NH-C_{20}H_{41}$ |
| " | " | " | " | " | " | $OC_4H_9$ | " | $OC_{10}H_{21}$ |
| " | " | " | " | " | " | " | " | $OC_{20}H_{41}$ |
| " | " | " | " | " | " | " | " | (1) |
| " | " | " | " | " | " | " | " | (3) |
| " | " | " | " | " | " | " | " | $NH-C_{20}H_{41}$ |
| " | " | " | (5) | $CH_3$ | " | $NH_2$ | n = 0 | $OC_{10}H_{21}$ |
| " | " | " | " | " | " | " | " | $OC_{20}H_{41}$ |
| " | " | " | " | " | " | " | " | (1) |
| " | " | " | " | " | " | $OC_4H_9$ | " | $OC_{10}H_{21}$ |
| " | " | " | " | " | " | " | " | $OC_{20}H_{41}$ |
| " | " | " | " | " | " | " | " | (1) |
| " | " | " | " | " | " | $NH_2$ | L-Ala | $OC_{10}H_{21}$ |
| " | " | " | " | " | " | " | " | $OC_{20}H_{41}$ |
| " | " | " | " | " | " | " | " | (1) |
| " | " | " | " | " | " | " | " | (3) |
| " | " | " | " | " | " | " | " | $NH-C_{20}H_{41}$ |
| " | " | " | " | " | " | $OC_4H_9$ | " | $OC_{10}H_{21}$ |
| " | " | " | " | " | " | " | " | $OC_{20}H_{41}$ |
| " | " | " | " | " | " | " | " | (1) |
| " | " | " | " | " | " | " | " | (3) |
| " | " | " | " | " | " | " | " | $NH-C_{20}H_{41}$ |
| " | " | " | " | H | " | $NH_2$ | n = 0 | $OC_{10}H_{21}$ |
| " | " | " | " | " | " | " | " | $OC_{20}H_{41}$ |
| " | " | " | " | " | " | " | " | (1) |
| " | " | " | " | " | " | $OC_4H_9$ | " | $OC_{10}H_{21}$ |
| " | " | " | " | " | " | " | " | $OC_{20}H_{41}$ |
| " | " | " | " | " | " | " | " | (1) |
| " | " | " | " | " | " | $NH_2$ | L-Ala | $OC_{10}H_{21}$ |
| " | " | " | " | " | " | " | " | $OC_{20}H_{41}$ |
| " | " | " | " | " | " | " | " | (1) |
| " | " | " | " | " | " | " | " | (3) |
| " | " | " | " | " | " | " | " | $NH-C_{20}H_{41}$ |
| " | " | " | " | " | " | $OC_4H_9$ | " | $OC_{10}H_{21}$ |
| " | " | " | " | " | " | " | " | $OC_{20}H_{41}$ |
| " | " | " | " | " | " | " | " | (1) |
| " | " | " | " | " | " | " | " | (3) |
| " | " | " | " | " | " | " | " | $NH-C_{20}H_{41}$ |
| $\phi NH_2$ | " | " | H | $CH_3$ | " | $NH_2$ | n = 0 | $OC_{10}H_{21}$ |
| " | " | " | " | " | " | " | " | $OC_{20}H_{41}$ |
| " | " | " | " | " | " | " | " | (1) |
| " | " | " | " | " | " | $OC_4H_9$ | " | $OC_{10}H_{21}$ |
| " | " | " | " | " | " | " | " | $OC_{20}H_{41}$ |
| " | " | " | " | " | " | " | " | (1) |
| " | " | " | " | " | " | $NH_2$ | L-Ala | $OC_{10}H_{21}$ |
| " | " | " | " | " | " | " | " | $OC_{20}H_{41}$ |
| " | " | " | " | " | " | " | " | (1) |
| " | " | " | " | " | " | " | " | (3) |
| " | " | " | " | " | " | " | " | $NH-C_{20}H_{41}$ |
| " | " | " | " | " | " | $OC_4H_9$ | " | $OC_{10}H_{21}$ |
| " | " | " | " | " | " | " | " | $OC_{20}H_{41}$ |
| " | " | " | " | " | " | " | " | (1) |
| " | " | " | " | " | " | " | " | (3) |
| " | " | " | " | " | " | " | " | $NH-C_{20}H_{41}$ |
| " | " | " | " | H | " | $NH_2$ | n = 0 | $OC_{10}H_{21}$ |

-continued

| $R_1$ | $R_2$ | $R_4$ | $R_6$ | R | X | Y | $-(A)_n-$ | Z |
|---|---|---|---|---|---|---|---|---|
| " | " | " | " | " | " | " | " | $OC_{20}H_{41}$ |
| " | " | " | " | " | " | " | " | (1) |
| " | " | " | " | " | " | $OC_4H_9$ | " | $OC_{10}H_{21}$ |
| " | " | " | " | " | " | " | " | $OC_{20}H_{41}$ |
| " | " | " | " | " | " | " | " | (1) |
| " | " | " | " | " | " | $NH_2$ | L-Ala | $OC_{10}H_{21}$ |
| " | " | " | " | " | " | " | " | $OC_{20}H_{41}$ |
| " | " | " | " | " | " | " | " | (1) |
| " | " | " | " | " | " | " | " | (3) |
| " | " | " | " | " | " | " | " | $NH-C_{20}H_{41}$ |
| " | " | " | " | " | " | $OC_4H_9$ | " | $OC_{10}H_{21}$ |
| " | " | " | " | " | " | " | " | $OC_{20}H_{41}$ |
| " | " | " | " | " | " | " | " | (1) |
| " | " | " | " | " | " | " | " | (3) |
| " | " | " | " | " | " | " | " | $NH-C_{20}H_{41}$ |
| H | " | " | " | $CH_3$ | " | $NH_2$ | Alaninol | $CO-C_{10}H_{21}$ |
| " | " | " | " | " | " | " | " | $CO-C_{20}H_{41}$ |
| " | " | " | " | " | " | " | " | $CO-(4)$ |
| " | " | " | " | " | " | " | " | $CO-(5)$ |
| " | " | " | " | " | " | $OC_4H_9$ | " | $CO-C_{10}H_{21}$ |
| " | " | " | " | " | " | " | " | $CO-C_{20}H_{41}$ |
| " | " | " | " | " | " | " | " | $CO-(4)$ |
| " | " | " | " | " | " | " | " | $CO-(5)$ |
| " | " | " | " | " | " | $NH_2$ | Ala-Alaninol | $CO-C_{10}H_{21}$ |
| " | " | " | " | " | " | " | " | $CO-C_{20}H_{41}$ |
| " | " | " | " | " | " | " | " | $CO-(4)$ |
| " | " | " | " | " | " | " | " | $CO-(5)$ |
| " | " | " | " | " | " | $OC_4H_9$ | " | $CO-C_{10}H_{21}$ |
| " | " | " | " | " | " | " | " | $CO-C_{20}H_{41}$ |
| " | " | " | " | " | " | " | " | $CO-(4)$ |
| " | " | " | " | " | " | " | " | $CO-(5)$ |
| " | " | " | " | " | L-Ser | $NH_2$ | Alaninol | $CO-C_{10}H_{21}$ |
| " | " | " | " | " | " | " | " | $CO-C_{20}H_{41}$ |
| " | " | " | " | " | " | " | " | $CO-(4)$ |
| " | " | " | " | " | " | " | " | $CO-(5)$ |
| " | " | " | " | " | " | $OC_4H_9$ | " | $CO-C_{10}H_{21}$ |
| " | " | " | " | " | " | " | " | $CO-C_{20}H_{41}$ |
| " | " | " | " | " | " | " | " | $CO-(4)$ |
| " | " | " | " | " | " | " | " | $CO-(5)$ |
| " | " | " | " | " | " | $NH_2$ | Ala-Alaninol | $CO-C_{10}H_{21}$ |
| " | " | " | " | " | " | " | " | $CO-C_{20}H_{41}$ |
| " | " | " | " | " | " | " | " | $CO-(4)$ |
| " | " | " | " | " | " | " | " | $CO-(5)$ |
| " | " | " | " | H | L-Ala | " | Alaninol | $CO-C_{10}H_{21}$ |
| " | " | " | " | " | " | " | " | $CO-C_{20}H_{41}$ |
| " | " | " | " | " | " | " | " | $CO-(4)$ |
| " | " | " | " | " | " | " | " | $CO-(5)$ |
| " | " | " | " | " | " | $OC_4H_9$ | " | $CO-C_{10}H_{21}$ |
| " | " | " | " | " | " | " | " | $CO-C_{20}H_{41}$ |
| " | " | " | " | " | " | " | " | $CO-(4)$ |
| " | " | " | " | " | " | " | " | $CO-(5)$ |
| " | " | " | " | " | " | $NH_2$ | Ala-alaninol | $CO-C_{10}H_{21}$ |
| " | " | " | " | " | " | " | " | $CO-C_{20}H_{41}$ |
| " | " | " | " | " | " | " | " | $CO-(4)$ |
| " | " | " | " | " | " | " | " | $CO-(5)$ |
| " | " | " | " | " | " | $OC_4H_9$ | " | $CO-C_{10}H_{21}$ |
| " | " | " | " | " | " | " | " | $CO-C_{20}H_{41}$ |
| " | " | " | " | " | " | " | " | $CO-(4)$ |
| " | " | " | " | " | " | " | " | $CO-(5)$ |
| " | " | " | " | " | L-Ser | $NH_2$ | Alaninol | $CO-C_{10}H_{21}$ |
| " | " | " | " | " | " | " | " | $CO-C_{20}H_{41}$ |
| " | " | " | " | " | " | " | " | $CO-(4)$ |
| " | " | " | " | " | " | " | " | $CO-(5)$ |
| " | " | " | " | " | " | $OC_4H_9$ | " | $CO-C_{10}H_{21}$ |
| " | " | " | " | " | " | " | " | $CO-C_{20}H_{41}$ |
| " | " | " | " | " | " | " | " | $CO-(4)$ |
| " | " | " | " | " | " | " | " | $CO-(5)$ |
| " | " | " | " | " | " | $NH_2$ | Ala-Alaninol | $CO-C_{10}H_{21}$ |
| " | " | " | " | " | " | " | " | $CO-C_{20}H_{41}$ |
| " | " | " | " | " | " | " | " | $CO-(4)$ |
| " | " | " | " | " | " | " | " | $CO-(5)$ |
| " | " | " | (4) | $CH_3$ | L-Ala | " | Alaninol | $CO-C_{10}H_{21}$ |
| " | " | " | " | " | " | " | " | $CO-C_{20}H_{41}$ |
| " | " | " | " | " | " | " | " | $CO-(4)$ |
| " | " | " | " | " | " | " | " | $CO-(5)$ |
| " | " | " | " | " | " | $OC_4H_9$ | " | $CO-C_{10}H_{21}$ |
| " | " | " | " | " | " | " | " | $CO-C_{20}H_{41}$ |
| " | " | " | " | " | " | " | " | $CO-(4)$ |
| " | " | " | " | " | " | " | " | $CO-(5)$ |
| " | " | " | " | " | " | $NH_2$ | Ala-Alaninol | $CO-C_{10}H_{21}$ |
| " | " | " | " | " | " | " | " | $CO-C_{20}H_{41}$ |

-continued

| R₁ | R₂ | R₄ | R₆ | R | X | Y | —(A)ₙ— | Z |
|----|----|----|----|---|---|---|--------|---|
| " | " | " | " | " | " | " | " | CO—(4) |
| " | " | " | " | " | " | " | " | CO—(5) |
| " | " | " | " | " | " | OC₄H₉ | " | CO—C₁₀H₂₁ |
| " | " | " | " | " | " | " | " | CO—C₂₀H₄₁ |
| " | " | " | " | " | " | " | " | CO—(4) |
| " | " | " | " | " | " | " | " | CO—(5) |
| " | " | " | " | " | " | NH₂ | Alaninol | CO—C₁₀H₂₁ |
| " | " | " | " | " | " | " | " | CO—C₂₀H₄₁ |
| " | " | " | " | " | " | " | " | CO—(4) |
| " | " | " | " | " | " | " | " | CO—(5) |
| " | " | " | " | " | " | OC₄H₉ | " | CO—C₁₀H₂₁ |
| " | " | " | " | " | " | " | " | CO—C₂₀H₄₁ |
| " | " | " | " | " | " | " | " | CO—(4) |
| " | " | " | " | " | " | " | " | CO—(5) |
| " | " | " | " | " | " | NH₂ | Ala-Alaninol | CO—C₁₀H₂₁ |
| " | " | " | " | " | " | " | " | CO—C₂₀H₄₁ |
| " | " | " | " | " | " | " | " | CO—(4) |
| " | " | " | " | " | " | " | " | CO—(5) |
| " | " | " | " | " | " | OC₄H₉ | " | CO—C₁₀H₂₁ |
| " | " | " | " | " | " | " | " | CO—C₂₀H₄₁ |
| " | " | " | " | " | " | " | " | CO—(4) |
| " | " | " | " | " | " | " | " | CO—(5) |

(1) 3-glyceryl-1-corynomycolate - $OC_{34}H_{63}O_{3,6}$
(2) 3-glyceryl-1-nocardomycolate - $OC_{54}H_{101}O_{3,6}$
(3) 3-glyceryl-1-mycolate - $OC_{90}H_{178}O_5$
(4) corynomycolyl - $C_{31}H_{57}O_{2,3}$
(5) mycolyl - $C_{87}H_{170}O_{2,3}$ The products according to the invention are prepared by synthesis. If necessary, certain of the "fragments" used for the syntheses can be derived from natural products.

To arrive at the same compound, various routes are possible. In all cases, the synthesis includes a series of steps in the course of which the various "fragments" constituting the structure of the whole of the compounds according to the invention are progressively assembled. The principal differences between the possible routes is situated in the sequence selected for the assembly of the fragments. The reaction methods leading to the fastening of one fragment to the one or more contiguous fragments are on the whole little modified by the order in which this integration is conducted, it being well understood that this order depends, on the one hand, on the selection of functional groups which react and which, consequently, must be freed for the step concerned, and on the other hand, the choice of the groups which must be blocked in order not to intervene in the course of this same step.

The preparation of the products according to the invention can be done from the corresponding compounds of the muramyl-peptide type. The production of the latter has been described in numerous publications. If necessary, for those whose preparation does not appear expressly in the literature, notably for the various modifications corresponding to the substitutions of the muramyl group or of similar groups, they can be obtained by following the conventional methods of preparation of corresponding derivatives of oligosaccharide chemistry.

In the same way, the constitution of the peptide chain connected to the muramic acid is carried out according to traditional methods in the synthesis of peptides.

Below are given in succinct manner the main indications relating to various operations which can be applied for synthesizing the products according to the invention, first by envisaging separately each step, then by indicating some preferred typical sequences.

(a) Formation of muramic acid or the like

To obtain the analogues of N-acetyl-muramic acid of the formula

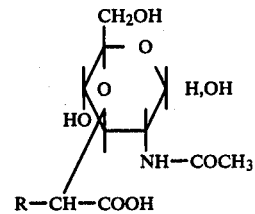

in which R has the previously indicated meaning, it is possible to start from a derivative of N-acetyl-2-glucosamine whose hydroxyls in position 1, 4 and 6 are blocked in a conventional manner. The method of preparation of such a derivative, the benzyl-2-acetamido-4,6-O-benzylidene-2-deoxy-D-glucopyranoside, is described notably by P.H. GROSS and R. W. JEANLOZ (J. Org. Chem. 1967, 32, 2761).

The formation of N-acetyl-muramic acid (R=CH₃) or of one of its analogues can be effected in the way described in French Patent Application Nos. 74 22909 or 76 19236 (respectively, for these applications, R=CH₃ and R=H) taking the metod described by OZAWA and JEANLOZ (J. Org. Chem., 1965, 30, 448).

This formation comprises for example the preparation of a sodium salt of the hydroxyl at the 3 position and the subsequent condensation of the sodium derivative with the salt or the ester of an α halogenated acid such as 2-chloro-propionic acid or chloroacetic acid to take up again the case of the two previously indicated patent applications. The halogen compound used in the L form can be prepared by the method described by SINAY et al (J. Biol. Chem., 1972, 247, 391). By using the appropriate halogenated acids, it is possible to prepare all the derivatives corresponding to the various significances of R. Thus, to introduce an R group with 4 carbons, the salts or esters of 2-chloro-butyric acid may be used.

When a halogenated acid ester is utilized, in order to be able to proceed with the subsequent peptide condensation, the carboxylic function may be freed by suitable hydrolysis.

(b) Substitution on the saccharide residue

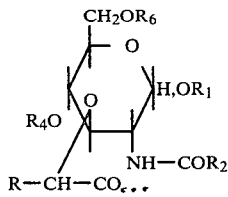

Starting from N-acetyl-muramic derivatives blocked in the 1, 4, 6 positions as obtained in (a), it is possible to prepare the various analogous compounds in which the acetyl group fixed to the nitrogen at the 2 position is replaced by substituents whose nature is that given in the general definition, that is, an alkyl, aryl or alkylaryl group, possibly substituted and including at most 22 carbon atoms. For this modification, it is possible to carry out in a known manner a hydrolysis of the acetyl by a strong base, for example, as is described in the publication of P. H. GROSS and R. W. JEANIOZ indicated above.

The resulting compound, in which an amino group is in the 2 position of the glucopyranoside ring, can then be again subjected to an acylation process, under the usual conditions, with a suitable acylating agent corresponding to the $R_2$ group that it is desired to introduce. As an acylating agent, it is possible notably to use the acid anhydrides or chlorides.

The substitutions at the 1, 4 and 6 position may be effected by methods which have been described previously and which are conventional in sugar chemistry. When the contemplated constituents are different from one another, as many successive substitution reactions follow as there are distinct substituents. In the course of these reactions, the positions which do not have to be substituted or those which must subsequently be the subject of another substitution are protected temporarily by blocking groups according to conventional methods.

The blocking groups initially present, in the case where one starts, as previously indicated, from benzyl-2-acetamido-4,6-O-benzylidene-2-deoxy-D-glucopyranoside, are removed, for example, by action of the acetic acid (at 60% for 1 hour under reflux) and catalytic hydrogenation, as described, for example, by MERSER et al. (Biochem. Biophy. Res. Commun., 1975, 66, 1316), or by catalytic hydrogenation by the method of LEFRANCIER et al. (Int. J. Peptide Protein Res., 1977, 9, 249).

The methods of substitution are those conventionally used. To obtain the acylated derivatives, or procedure with the aid of an acylating agent corresponding to the substituent that it is desired to introduce (anhydride, acyl chloride, etc.) may be utilized.

The 1, 4, 6 positions are not equivalent as regards their reactivity. The $C^6$ position is easier to substitute, also, when this position must be substituted, it is possible to operate without blocking the other positions, with an amount of substitution agent equal to that necessary for the substitution in a single position.

A particular example of the method of preparation of the derivatives substituted at the 6 position is given in the article of KUSUMOTO et al. (Tetrehedron Letters, 1976, 47, 4237).

The substitutions on the oside residue may be produced before or after fixing the peptide chain or the fragments of the latter.

(c) Peptide chain

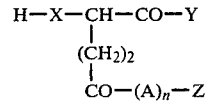

The fixing of a peptide chain to the N-acetylmuramic acid, or to an analogue of the latter as has been indicated above, is effected by traditional methods in the field of peptide synthesis. Such methods have been amply described in the prior literature and in particular in the previously indicated French patent applications.

In general, glycopeptide syntheses can be effected either by fixing a first amino acid to the muramyl group, then by fixing to the compound thus obtained the second amino acid, and so on. It is also possible to prepare the entire peptide chain separately amino acid by amino acid and to fix the latter on the muramyl group. It is finally possible to select intermediate methods in which fragments of the chain are prepared, and then these fragments are joined together until a complete chain is formed which is then fixed to the muramyl group, or to fix a first fragment to the muramyl group, then a second to the product thus obtained, etc. The choice of sequence is guided mainly by reasons of convenience or of yield.

The Y and Z substitutions are advantageously effected on the glutamyl group before the synthesis of the chain. In the same way, when n is different from O, that is, when one or several aminoacyl groups complete the peptide chain, the Z group is first fixed to the terminal aminoacyl before the latter is integrated into the peptide chain.

The peptide syntheses are carried out by conventional methods. By way of example, it is possible to use methods of activating carboxyls, like the metod called mixed anhydrides. Advantageously, the peptide synthesis is carried out by means of a compound of the carbodiimide type such as N,N'-dicyclo-hexylcarbodiimide or equivalent carbodiimides. A review of the conventional methods of peptide synthesis is to be found in J. H. JONES, Chemistry and Industry, 723 (1974). It is also possible to refer to the already mentioned French patent applications, or again to the following French patent applications: 75 29624, 76 06819, 76 06820, 76 06821, 76 21889, 77 02646 and to the article of LEFRANCIER et al. (Int. J. Peptide Protein Res., 1977, 9, 249 and 1978, 11, 289).

The formation of esterified or amidated derivatives corresponding to the group Y is obtained in a known manner. It is possible, in particular, to refer to the above-indicated French patent applications, and notably to French Applications 76 06820, 76 21889 and 77 02646.

To fix the residue Z to the amino acid situated at the end of the peptide chain, one proceeds with activation of the carboxylic group of the amino acid in a known manner, and it is subjected to alcoholysis or aminolysis by an R'OH alcohol or an R'NH2 amine.

(d) Synthesis sequence of glycopeptide compounds corresponding to the modification of the general formula in which n is 1 or 2

Diagram (I) shows a typical sequence of reactions ending in the production of peptide derivatives corresponding to the portion $(A)_n$—Z of the general formula I.

An activated ester BOC-$A_1$-OR″ (succinimide ester, p-nitrophenyl ester, etc.) of an N-protected amino acid (like for example the ter butyloxycarbonyl denoted by LE-BOC, or indeed any other suitable temporary group for the amine function, used in peptide synthesis) is subjected, either to alcoholysis by an alcohol with a chain of more than 4 carbons in the presence of imidazole as catalyst (as indicated by BONDANZKY et al. J. Org. Chem., 1977, 42, 149), however, in the case where $R'_1$ is an alkyl group with a chain of 4 to 20 carbons, the known conventional methods of esterification of the amino acids are advantageously used, or to aminolysis by an alkyl amine with a chain of more than 4 carbons. Once the acyl-aminoacyl-alkyl ester or acyl-aminoacyl-alkyl amide respectively are obtained, freed from the N-protected acyl group (for example, for ter-butyloxycarbonyl, by a N solution of hydrochloric acid in glacial acetic acid), one obtains a compound or formula ($A_1$-$Z_1$) or ($A_1$-$Z_2$). The product obtained may be coupled by known methods of peptide synthesis with a second acyl amino acid to give, after removal of the N-protecting acyl group used, a dipeptide compound of the formula $A_2$-$A_1$-Z.

To prepare the compounds according to the invention in which the last residue of $(A)_n$ corresponds to an aminoalcohol, it is possible to operate according to a modification of the preceding sequence shown by the diagram (I′).

For this modification, an N-protected derivative of an amino acid such as BOC-A′-COOH is selectively reduced to its aminoalcohol derivative BOC-A′-CH$_2$OH according to well-known methods. The amino acid can also be reduced in the same manner to its corresponding aminoalcohol, then selectively acylated at its amine function according to currently used methods in peptide synthesis. The alcohol function thus formed can then be esterified by an activated ester (succinimide ester, p-nitrophenyl ester, etc.) of a fatty acid with a chain of more than 4 carbons ($R'_1$-CUOR″), in the presence of imidazole used as catalyst (as indicated in BONDANZKY et al., J. Org. Chem., 1977, 42, 149). This ester may also be formed from the chloride, from the anhydride or from the imidazolide of the fatty acide. The sequence of the reactions is essentially that described above for the modification of diagram (I).

Diagram (II) represents the reaction sequences leading to the production of glycopeptide derivatives. One starts with a derivative (1) with $R_1$ a benzyl radical, as described by GROSS and JEANLOZ (J. Org. Chem., 1967, 32, 2759). To obtain the compound in which $R_1$ is an alkyl or aryl-alkyl group, one may use the method of preparation corresponding α- or β-glycosides also described in this same article, or any known method for such preparations in the chemistry of oligosaccharides.

If it is desired to modify the nature of the N-acyl group, the N-acetyl group can be hydrolysed as described by GROSS and JEANLOZ, to result in the derivatives of formula (2). The derivatives (2) can then be N-acylated selectively by the action of the anhydride of carboxylic acids to result in derivatives of formula (3). The derivatives of formula (4) can be obtained from the preceding ones by the method described by OZAWA and JEANLOZ (J. Org. Chem., 1965, 30, 448), by means of an L-α-chloroalkanoic acid.

The derivatives of formula (4) are coupled with a dipeptide derivative of the general formula H-X-D-Glu (OBzl)-OY, hydrochloride. In which formula X corresponds to an amino acid, and Y, for example, to an amino-, hydroxy-, methylamino-, methoxy- or glycylamide radical. These various peptide derivatives are prepared according to methods described by LE-FRANCIER et al. (Int. J. Peptide Protein Res., 1977, 9, 249, and Int. J. Peptide Protein Res., 1978, in press). The coupling methods used to obtain the glycopeptide derivatives of formula (5) are also described in the previously cited articles. However, both in the synthesis of the dipeptide derivatives and in that of the derivatives of formula (5), any coupling method used in peptide synthesis may be used.

Catalytic hydrogenation of the compounds of formula (5) is carried out in traditional manner (LEFRANCIER et al., Int. J. Peptide Protein Res., 1977, 9, 249) to produce compounds of formula (6).

The derivatives of formula (6) are coupled, for example, by the method described below in detail for the modification (point d), (page 36) of the preparation of the decyl ester of MDP-L-alanine, by means of a carbodiimide and hydroxy-benzotriazole, with one of the derivatives of the general formula H-$(A)_n$-Z hydrochloride of which the diagram (I) gives the synthesis sequence. Compounds of formula (7) are obtained.

In a modification, the derivatives of formula (5) undergo selective debenzylidenation as described by MERSER et al. (Biochem. Biophys. Res. Commun., 1975, 66, 1316) to give the derivatives of formula (8). Selective acylation of the primary hydroxyl at the 6 position of the saccharide residue can then be done directly by the action of a slight excess of carboxylic or acyl-imidazole acid anhydride. Derivatives of formula (9) are obtained.

The derivatives of formula (9) can be synthesized by a totally different sequence (diagram IV, formula 4) similar to that developed by KUSUMOTO et al. (Tetrahedron Letters, 1976, 47, 4237), from specific tosylation of the primary alcohol of the saccharide residue.

After catalytic hydrogenation of the compounds (9), carried out as usual in the presence of 5% palladium on charcoal, the compounds of formula (10) are obtained to which, as previously, may be coupled a residue to give the compound (11) according to the invention.

In another modification, the derivatives of formula (8) are diacylated on the two hydroxyls in the 4 and 6 positions of the saccharide residue by the action of an excess of carboxylic acid anhydride, then subjected to a conventional catalytic hydrogenation such in the presence of 5% palladium on carbon, to obtain compounds of formula (13). After coupling with the residue $(A)_nZ$, as described previously, the compounds (14) according to the invention are obtained.

(e) Synthesis sequences of glycopeptide compounds corresponding to the embodiment of the general formula in which n is zero When n=0, the γ-carboxyl function of the D-glutamyl residue is engaged in an ester linkage with an alcohol having a chain of more than 4 carbons.

A particular method for preparing these derivatives consists of making the γ-p-nitrophenyl ester of the blocked peptide fragment BOC-X-D-Glu-O-Y, then proceeding with alcoholysis by an alcohol with a chain of more than 4 carbons in the presence of imidazole as catalyst (as indicated by BODANZKY et al., J. Org. Chem., 1977, 42, 149). After the usual acidolysis of the ter-butyloxycarbonyl group, the derivative obtained is coupled with a suitable saccharide derivative corresponding to the formula (1) (Diagram III) to result in derivatives of the formula (2) according to the method described below in detail at points (a), (b) and (c) for the preparation of the decyl ester of MDP-L-alanine or according to the methods described in MERSER et al. (Biochem. Biophys. Res. Commun., 1974, 466, 1316), LEFRANCIER et al. (Int. J. Peptide Protein Res., 1977, 9, 249, and Int. J. Peptide Protein Res., 1978, 11, 289). After catalytic hydrogenation and purification carried out as described in the two last articles cited, the compounds of formula (3) are obtained. In a modification, the derivatives of formula (2) undergo selective debenzylidenation as described by MERSER et al. (Biochem. Biophys. Res. Commun., 1975, 66, 1316) to give the derivatives of formula (4).

Selective acylation of the primary hydroxyl at the 6 position of the saccharide residue can be done directly by the action of a slight excess of the anhydride, or of the acyl-imidazole of carboxylic acid. The derivatives of formula (5) are thus prepared (if $R_1$ is the benzyl radical, it may be removed by catalytic hydrogenation carried out as usual in the presence of 5% palladium on carbon). These derivatives may be synthesized by a totally different sequence (Diagram IV, formula (5)) similar to that developed by KUSUMOTO et al. (Tetrahedron Letters, 1976, 47, 4237).

In another embodiment, the derivatives of formula (4) are diacylated on the hydroxyls at position 4 and 6 of the saccharide residue by the action of an excess of carboxylic acid anhydride to produce finally the compound of the formula (7), subjected, if necessary, to conventional catalytic hydrogenation in the presence of 5% palladium on carbon, if $R_1$ is initially a benzyl protection radical.

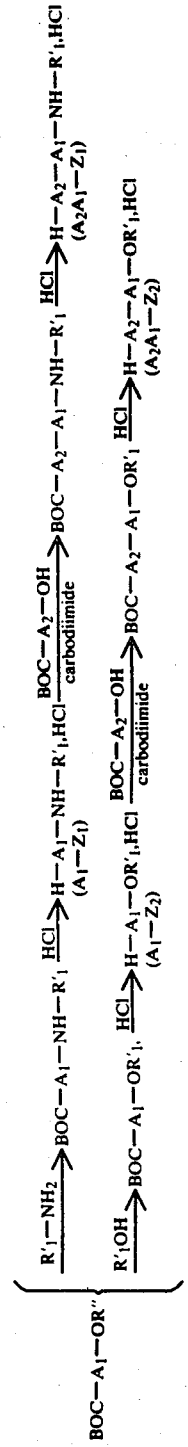
DIAGRAM (I)
REACTION SEQUENCE OF THE PREPARATION OF PEPTIDE DERIVATIVES
OF FORMULA $(A)_n-Z$ with $n = 1$ or $2$

DIAGRAM (I')
REACTION SEQUENCE OF THE PREPARATION OF PEPTIDE DERIVATIVES
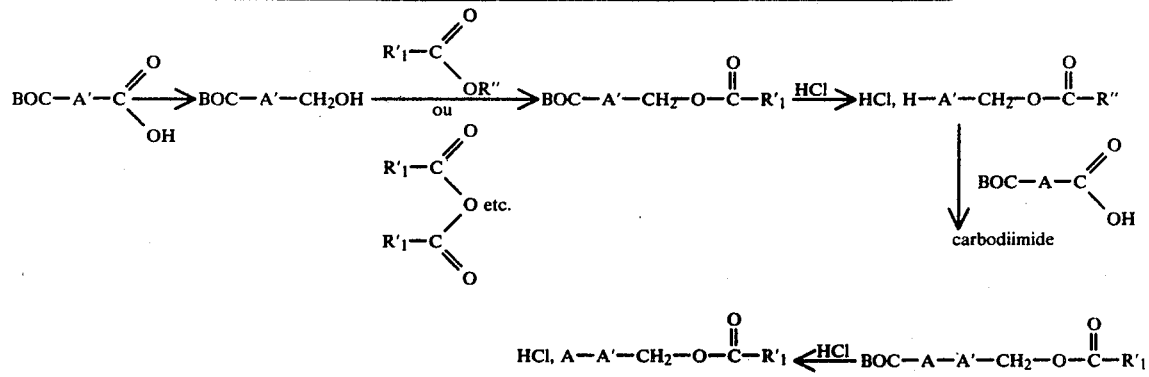

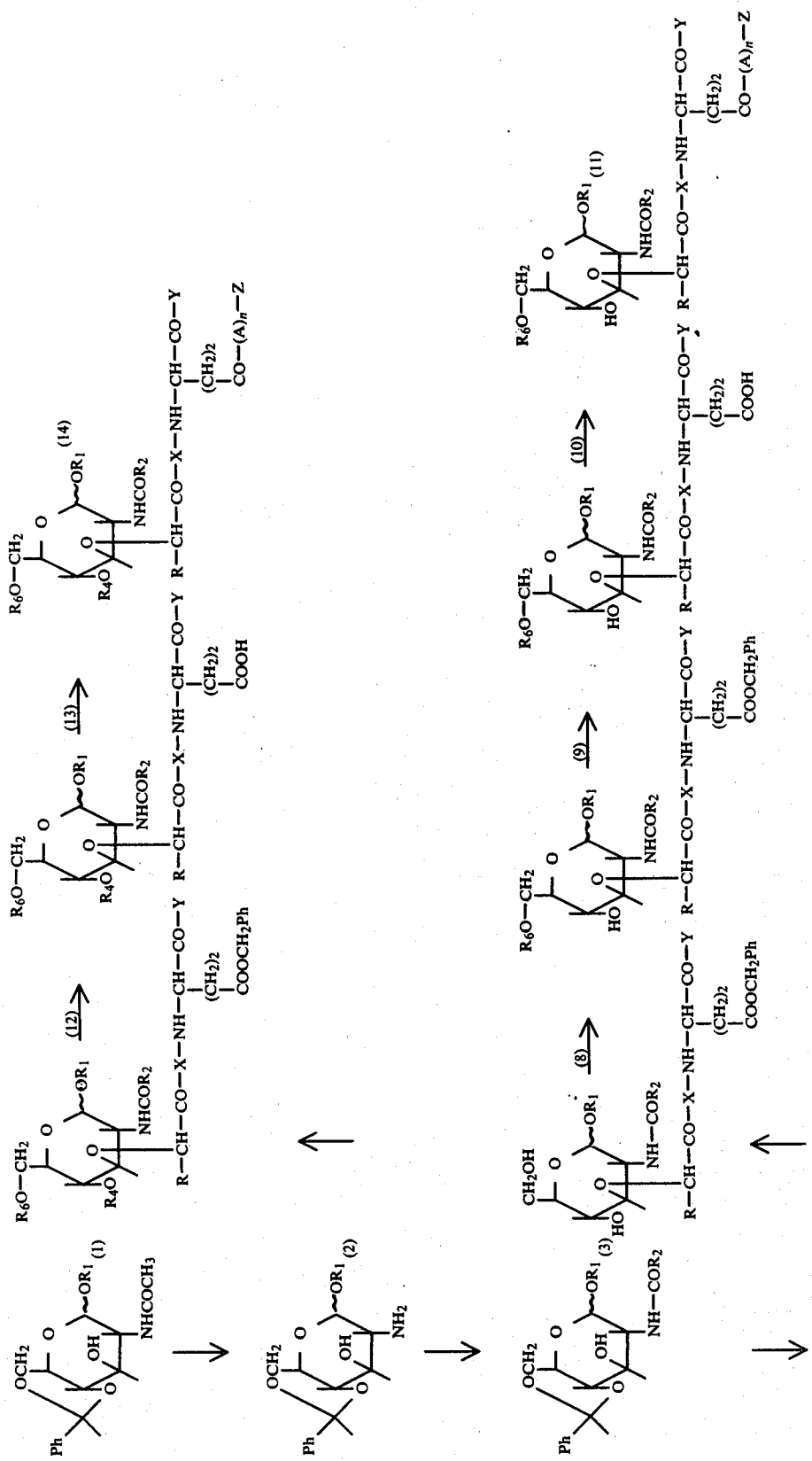

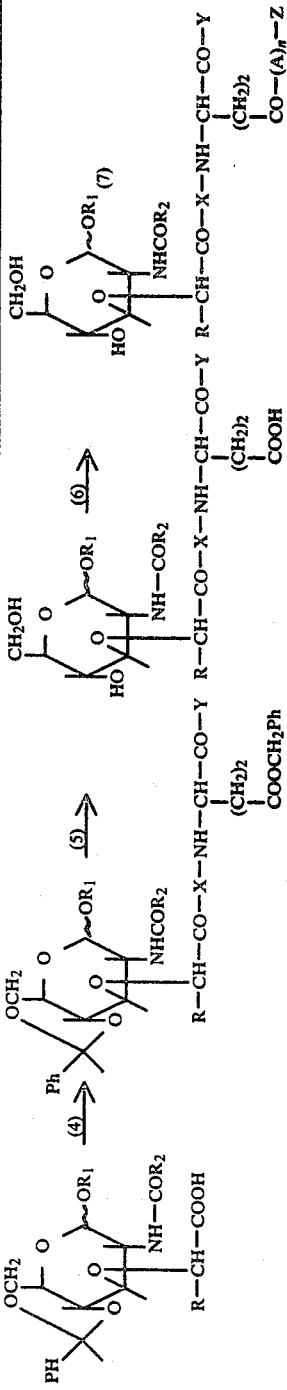

DIAGRAM (III)
SYNTHESIS SEQUENCES OF GLYCOPEPTIDE COMPOUNDS CORRESPONDING TO THE VARIATION OF THE GENERAL FORMULA in which n is zero
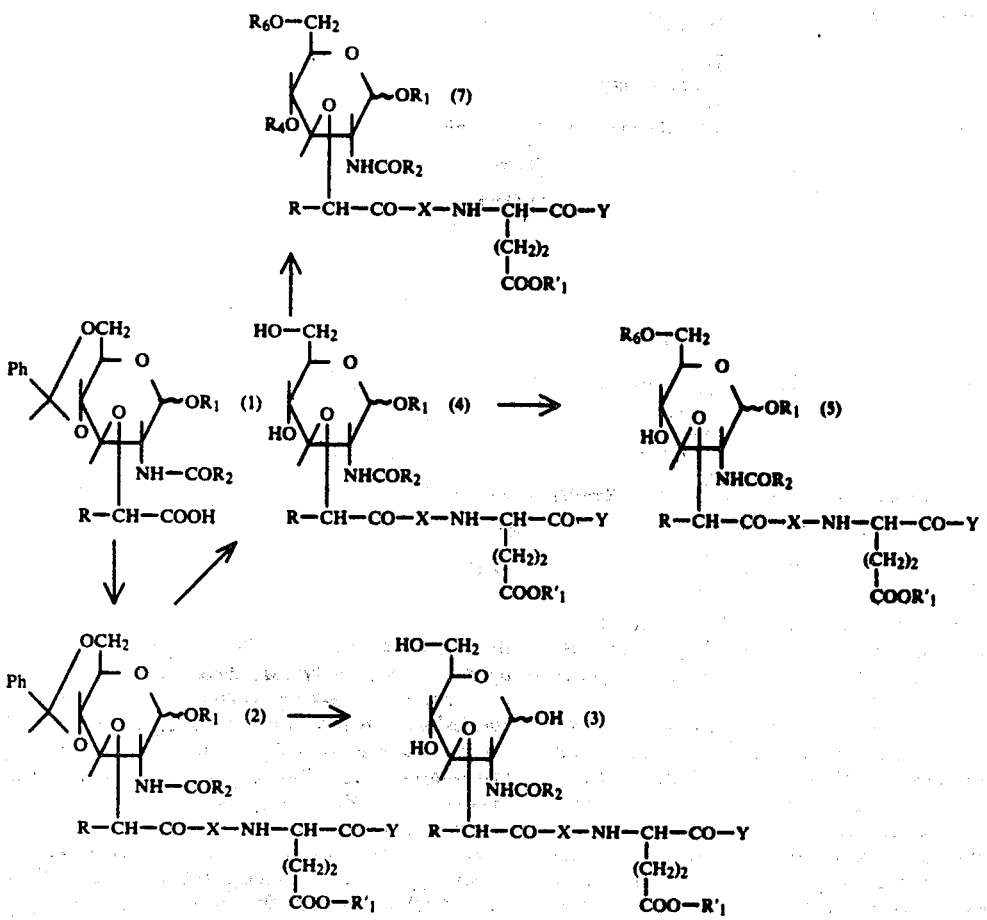
DIAGRAM (IV)
SYNTHESIS SEQUENCE FOR GLYCOPEPTIDE DERIVATIVES CORRESPONDING TO THE GENERAL FORMULA AND OF WHICH THE C6 HYDROXYL OF THE SACCHARIDE RESIDUE IS ACYLATED BY A LONG CHAIN FATTY ACID
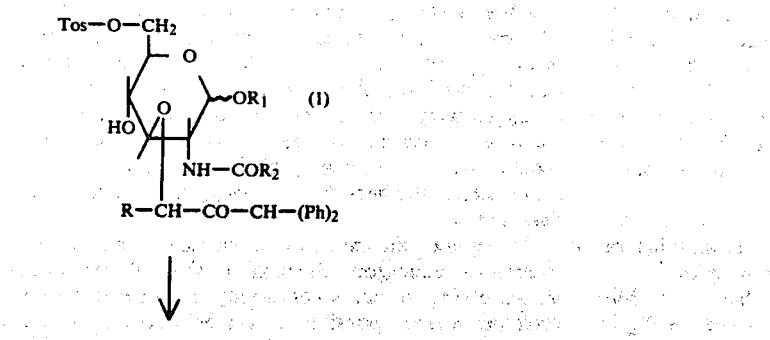

DIAGRAM (IV)
SYNTHESIS SEQUENCE FOR GLYCOPEPTIDE DERIVATIVES, CORRESPONDING TO THE GENERAL FORMULA AND OF WHICH THE C6 HYDROXYL OF THE SACCHARIDE RESIDUE IS ACYLATED BY A LONG CHAIN FATTY ACID

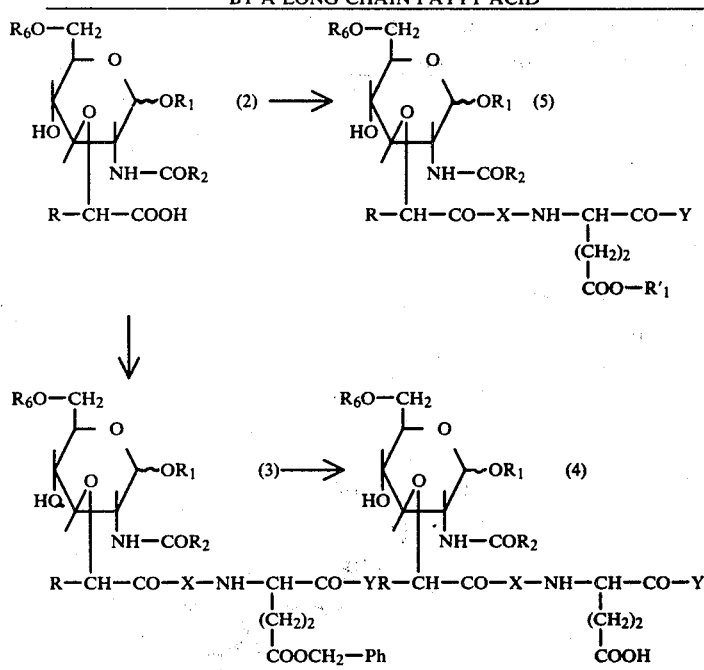

The invention also relates to methods of using the compounds corresponding to the preceding definitions, notably as a reactant or as an active substance in pharmaceutical compositions.

The invention relates to biological reactants, for example standard immunological adjuvants, which can be constituted by means of the compounds according to the invention, notably in order to study the possible adjuvant properties of the substances under investigation, by comparison with such standard adjuvants or, on the contrary, as an agent capable of countering certain effects connected with the administration of immunosuppressive substances.

More particularly, the invention relates to medicaments including as active principle at least one of the compounds according to the invention, this medicament being applicable to control immune responses of the subject to which it is administered.

These medicaments are notably applicable when a reinforcement of the immunitary response to any immunogenic agent is sought. Such immunogenic agents may be natural or synthetic, and necessitate the use of a stimulating agent for the immunitary system, whether the immunogenic agent is weak in nature or whether it is strong and can be used at very small dose, or again if the immunogenic character has been reduced, for example in the course of modifications or prior purifications. In general, the utilization of the immunoregulator compounds according to the invention is useful each time that the immunogenic agent does not permit the induction of a sufficient response.

The invention relates more particularly to the application of the compounds concerned to the amplification of the immunogenic effect of active principles of vaccines administered to a host, animal or human, notably in the case where these vaccinating principles belong to the above-mentioned immunogenic categories of agents. Consequently, the invention relates also to pharmaceutical compositions whose active principle is constituted by at least one of the compounds according to the invention, in association with the appropriate pharmaceutical vehicle for the mode of administration required or useable having regard to the nature of the vaccinating principle used.

The invention is applied in particular to those vaccinating agents whose immunogenic character is strong but which are difficult for use in normal times by reason of too high a toxicity or undesirable side-effects. It has been confirmed that the adjuvant agents according to the invention are capable of effectively compensating for the loss in immunogenic effect which would result normally from dilution or from reduction of the doses used, notably for the purpose of reducing the toxicity or the side-effects of the abovesaid agents to a corresponding degree, and this without unfavorably influencing the latter phenomena.

The same effects are observed in the case of strong vaccinating agents of which the immunogenic character has been reduced, notably by extensive purification, to the extent where this becomes necessary for the corresponding reduction of their toxic effects or injurious secondary effects. This is particularly the case for vaccinating principles constituted by bacterial anatoxins or viral anatoxins or, generally, vaccinating principles constituted by a part only of the constituents initially contained in the bacteria or virus against which protection is sought.

In general, the invention is applied to any antigen which has undergone chemical or physical transformations seeking to remove or modify the parts of the antigen which are responsible for its troublesome secondary effects whilst preserving the portions which are the cause of its immunogenic properties. It is to this type of weak immunogen that are attached, for example, the principles constituted by the "sub-units" derived from flu virus, and which retain only the hemagglutinines and the neuraminidases of the latter, to the exclusion of the nucleoproteins and other nucleotide constituents of the virus from which they are derived. This applies also to certain anatoxins, such as those, for example, of diphtheria or of tetanus, which, as is known, may be constituted by soluble substances, such as obtained by the simultaneous action of formaldehyde and of heat on bacterial toxins derived from the corresponding bacteria.

The invention also relates to the application of the compounds according to the invention for the treatment of infectious diseases. In this application, it must be noted that the products according to the invention are clearly distinguished from the customarily used antibiotics. The products according to the invention, contrary to antibiotics, do not have a bactericidal or bacteriostatic effect in vitro. On the other hand, they can activate isolated macrophages in vitro and their action in vivo is demonstrated as will be seen in the pharmacological test examples. Unlike the antibiotics again, the action is not limited to certain varieties of micro-organisms. This is explained, as we have seen, by the fact that their activity is not direct but develops through the nonspecific immunitary defense mechanisms of the host, which mechanisms their administration stimulates and amplifies. This difference in action with respect to antibiotics renders these products all the more advantageous as they can be used against pathogenic germs which have become resistant to antibiotics.

As has been seen, the mode of action of the products according to the invention approaches that of known antiinfectious compounds such as BCG or the lipopolysaccharides and since they can be employed with success for the treatment of infections without presenting the drawbacks, notably of toxicity, which limit or prevent the use of LPS or of BCG.

The application of the products according to the invention includes both the treatment of diseases caused by extracellular growth micro-organisms such as Klebsiella (or again notably Pseudomonas, staphylococci, streptococci) and that of micro-organisms with intracellular growth (Listeria, mycobacteria, corynobacteria...).

The applications indicated previously by way of examples are not exclusive of other applications bringing into action the immunoregulator properties of the compounds according to the invention. There can also be cited by way of example, their reinforcing action at the level of this specific immunization of the host with regard to parasitic antigens, the restoration of the immunocompetence of the host, when the latter is at a lower level than normal, notably when the latter has been damaged by the antigens or parasites themselves, or under the effect of chemotherapy, radiotherapy, or any other treatment having an immunosuppressive action.

The pharmaceutical compositions according to the invention, generally, are useful for the treatment or the prevention of infectious diseases of bacterial or parasitic origin, or for the inhibition of tumoral diseases.

The adjuvants according to the invention can be administered to the host—animal or human being—in any suitable manner for producing the desired effect. Administration of the immunoregulator principle, notably adjuvant, and of the immunogen agent, notably vaccinating antigen, can be contemplated simultaneously or separately, in the latter case if necessary staggered in time, if necessary again by similar or different routes of administration (for example parenteral and oral routes respectively or vice versa).

The invention relates naturally also to the various pharmaceutical compositions with which the compounds according to the invention can be incorporated, if necessary in association with other active substances. In particular, the compounds I are advantageously associated with immunogen agents, where, for example, immunogenic agents used at very low doses, or weak immunogenic agents, are concerned.

Advantageous pharmaceutical compositions are constituted by injectable solutions or suspensions containing an effective dose of at least one product according to the invention. Preferably, these solutions or suspensions are formed in an isotonic sterilized aqueous phase, preferably saline or glucosed.

The invention relates more particularly to such suspensions or solutions which are suitable for administration by intradermal, intramuscular, or sub-cutaneous injection, or again by scarification and notably pharmaceutical compositions in the form of liposomes whose constitution will be explained below.

It relates also to pharmaceutical compositions administerable by other routes, notably by the oral or rectal route, or again in the form of aerosols designed to be applied to the mucous membranes, notably the ocular, nasal, pulmonary or vaginal mucous membranes.

In consequence, it relates to pharmaceutical compositions in which one at least of the compounds according to the invention is associated with pharmaceutically acceptable excipients, solid or liquid, adapted to the constitution of oral, ocular or nasal forms, or with excipients adapted for the constitution of rectal forms of administration, or again with gelatinous excipients for vaginal administration. It relates also to isotonic liquid compositions containing one at least of the products according to the invention, adapted for administration to the mucous membranes, notably the ocular to nasal mucous membranes.

It relates lastly to compositions formed of pharmaceutically acceptable liquified gases, of the "propellant" type, in which the products according to the invention are dissolved or held in suspension, and of which the release causes the dispersions in an aerosol.

The invention consists also of a method of treatment aimed at reinforcing the immunitary defenses of the host, consisting of administering to said host an effective dose of one at least of the products according to the invention, in one of the administerable forms which have been mentioned above. By way of example of doses capable of inducing an effect, may be mentioned doses of 10 to 1,000 $\mu$g per kg of body weight, for example of 50 $\mu$g, when the administration is effected by the parenteral route, or again of a dose of 200 to 20,000 $\mu$g per kg body weight, for example of 1,000 $\mu$g, for other methods of administration, such as for example the oral route.

Besides the compounds themselves, the full importance of the form in which the compounds are used for exerting their immunoregulator properties is already known. Water in oil emulsions have been the first vehicles proposed for the administration of this type of product. However, the preparation, and especially the utilization of these emulsions raises difficulties. Thus, when the oily phase is not metabolizable, the injection of the composition can lead to undesirable local reactions.

The discovery of the activity of the compounds in the absence of an oily phase has constituted a remarkable advance by the suitability of administration which results therefrom in the absence of troublesome side-effects. However, the passage from the water in oil emulsion forms into forms characteristic of the active compounds in the absence of an oily phase, and notably aqueous solutions, can modify a certain aspect of the activity of the products concerned.

In this order of ideas, the "active" compounds in the absence of an oily phase present notably very interesting adjuvant properties as regards immunitary protection with humoral mediation.

It seems at the present time that the administration of these products in the absence of an oily phase does not permit the same results to be produced as in their administration in emulsion as regards the immunitary responses of the type of those that have been demonstrated, for example, by delayed hypersensitivity reactions.

Studies have shown that a suitable means for modifying the activity spectrum of the products of the muramyl-peptide type is to use them in the form of liposomes (which technique has been described notably for the administration of enzymatic preparations).

The liposomes, as is known, are generally produced from phospholipids or other lipid substances and are formed by mono or multilamellar hydrated liquid crystals. They are customarily used in dispersions in an aqueous medium.

It has thus been observed that the liposome forms could result in an increase in the anti-infectious activity in the tests carried out according to the procedure described below to detect activity with respect to Klebsiella infection. It has also been possible, in certain cases, to obtain an increase in the immunitary responses of the humoral and/or cellular mediation type.

The variations which result through the utilization of the liposome form are not necessarily oriented in the direction of a general increase in the activities of the product concerned. The essential point is, from a given product, to be able to obtain a whole range of properties as a function of the desired result, by selecting the most appropriate form.

As has been indicated above, pharmaceutical compositions according to the invention which are particularly advantageous are in the form of liposomes.

To form the liposomes, procedure is conventional. Any non-toxic, physiologically acceptable and metabolizable lipid, capable of forming liposomes, can be used.

The most usual lipids are the phospholipids, and notably the phosphatidyl-cholines (lecithins) both natural and synthetic. Phospholipids may also be used and among the latter notably are the phosphatidyl-serins, the phosphatidyl-inositides or the sphingomyelines. Other lipids can also be used, which have been described notably by W. R. HARGREAVES and D. W. DEAMER (Conference on liposomes and their Uses in Biology and Medicine, Sept. 14–16, 1977, New York Acad. Sci.) and in the article of Biochem., 1978, 18, p. 3759.

Traditional techniques and apparatus can be employed to form the liposomes according to the invention. These techniques have been described notably in Chapter IV of the work entitled "Methods in cell biology", edited by David M. PRESCOTT, Volume XIV, 1976, Academic Press, New York, page 33 et seq.

Advantageously, the initial dispersion is obtained from a thin film of lipid formed on the wall of a container from a solution of these lipids which had previously been introduced into this container and after evaporation of the solvent. The aqueous phase is then introduced into the container and the dispersion of the lipids into the midst of the aqueous solution is produced by stirring the medium, and generally by resorting to ultrasonic treatment.

In the first step there is obtained a suspension of liposomes having a milky appearance. It seems that, at this stage, the liposomes are formed of a series of concentric lipidic double layers alternating with aqueous compartments.

The liposomes thus obtained may be separated from the aqueous medium, for example by centrifugation. The liposomes contained in the centrifugation culot can then be washed, so as to remove any active substances not incorporated with the liposomes. The latter may then be resuspended in the buffer solution, in which they can be preserved, notably in the cold, preferably at a temperature of $+4°$ C. Such liposomes are stable for long periods.

Preferably, the initial lipid composition contains also a stabilizing agent, for example cholesterol. If necessary, recourse may also be had to an amphiphile agent, which may be added to the initial lipid dispersion in order to permit the final production of electrical charge carrying liposomes. Such agents comprise for example dicetylphosphate or phosphatidyl-serine, to the extent that it is desired to obtain negatively charged liposomes, or stearylamine, if it is desired to obtain positively charged liposomes.

Advantageously one starts from lecithin and from cholesterol. Generally, after having formed a film of lecithin-cholesterol in a container, a buffer aqueous solution is added and it is shaken to obtain a dispersion of the lipid film in the aqueous phase resulting in the formation of liposomes. The muramyl-peptide type compound, according to its solubility characteristics, is introduced either with the lipid phase (lecithin-cholesterol), or in the buffer aqueous solution.

The molar proportions of the constituents of the lipid phase are advantageously comprised between 8:1 and 1:1 (lecithin/cholesterol).

Advantageously, the aqueous phase is buffered so that its pH is close to neutrality. A buffer solution, for example, phosphate-NaCl 0.9% is used.

The liposome form compositions according to the invention can include other substances compatible with this particular form. They can notably, constitute vaccinating compositions, contain immunogen agents.

Generally, the compositions in the form of the liposomes can contain, in addition to the compound of the muramyl-peptide type, any constituents: stabilizers, preservatives, excipients or other active substances capable of being used in the injectable solutions or emulsions presented previously for administration of muramyl-peptide compounds, provided that they are compatible with this liposome form.

Contents of the order of 1 mg of muramyl-peptide per 35 mg of lipids are advantageously used.

The reasons for which the liposome forms lead to different results from those that are obtained from the preparations in the form of water in oil emulsions or in the form of solutions are not fully known. One may offer some hypotheses on the more precise nature of this. Thus the absence of troublesome reactions, which appear at the point of injection when water in oil emulsions (mineral oil) are used and this in spite of the presence of lipid constitutents, may reasonably be explained by the fact that the latter are metabolizable by nature.

The invention is described in more detail in the examples which follow relating to the preparation of products according to the invention, of a method of preparing the "liposome" pharmaceutical form, and various tests relating to the pharmacological properties of these products and of this particular form.

PREPARATION OF PRODUCTS ACCORDING TO THE INVENTION (1) Decyl ester of N-acetyl-muramyl-L-alanyl-D-isoglutaminyl-L-alanine (a) Decyl ester of L-alanine, paratoluene sulphonate 3 g of L-alanine, 30 ml of n-decanol and 6.54 g of paratoluene sulphonic acid (monohydrate) are mixed in a 250 ml flask. This flask is heated carefully over a bare flame of a bunsen burner until boiling of the n-decanol and the production of a homogeneous solution. To this still warm solution is then added, carefully, 100 ml of boiling benzene. The resulting solution is refluxed for 55 hours in a Soxhlet apparatus whose cartridge contains magnesia. The solution is then concentrated to remove the benzene, then the excess decanol is evaporated under high vacuum at 100° C. The reaction mixture is then cooled to 0° C., and the crystalline paste obtained is triturated with cold ether. The crystalline precipitate is rapidly drained and rinsed with cold ether. 1.71 g of paratoluene sulphonate of the decyl ester of L-alanine is obtained. This product has the following characteristics:

m.p. 65°–66° C.

The elementary analysis is:

| for $C_{20}H_{35}NO_5S$ (401.567) | C | H | N |
|---|---|---|---|
| Calculated: | 59.82 | 8.79 | 3.49 |
| Found: | 59.97 | 9.02 | 3.36 |

Evaporation of the mother liquor to dryness under vacuum provides 6.66 g of the same product probably still containing n-decanol.

(b) Decyl ester of L-alanyl-D-isoglutaminyl-L-alanine, hydrochloride

To 350 mg of the product prepared at (a), dissolved in 5 ml of dimethylformamide at −10° C., are added 100 μl of N-methylmorpholine. To this solution, are successively added 317 mg of t-butyloxycarbonyl-L-alanyl-D-isoglutamine, obtained by the method described by Lefrancier P. and Bricas E., (Bull. Soc. Chim. Biol., 1967, 49, 1257), 135 mg of hydroxy benzotriazole and 178 mg of dicyclohexylcarbodiimide. The reaction mixture is stirred for 24 hours at room temperature. The latter is then evaporated to dryness, and then the dicyclohexylurea is precipitated with dichloromethane. The solution is then filtered, the filtrate is washed successively with a solution of citric acid (10%) with water, with an N solution of sodium bicarbonate and with water. After evaporation to dryness of the organic phase, 307 mg of raw product are obtained. This product is dissolved in a minimum volume of dimethylformamide, and then passed through a column (2×10 cm) of Amberlyst 15 (H+) previously equilibrated with dimethylformamide. After evaporation to dryness of the eluate, 275 mg of decyl ester of BOC-L-alanyl-D-isoglutaminyl-L-alanine are obtained.

The whole of this product is then treated with 2 ml of hydrochoric acid (1 N solution in acetic acid) for 30 minutes. The solution is evaporated to dryness under vacuum, the residue is rinsed several times with acetone and the acetone is evaporated until the disappearance of the acetic odor. The resulting product is taken up again with water, ultrafiltered, then freeze-dried. 206 mg of the hydrochloride of the decyl ester of L-alanyl-D-isoglutaminyl-L-alanine are obtained. This product has a rotatory power of $[\alpha]_D = -14.7°$ (water).

Its elementary analysis is:

| for $C_{21}H_{41}N_4O_5Cl$ (465.04) | C | H | N |
|---|---|---|---|
| calculated: | 54.23 | 8.89 | 12.05 |
| found: | 54.15 | 8.93 | 11.31 |

(c) Decyl ester of N-acetyl-muramyl-L-alanyl-D-isoglutaminyl-L-alanine (Mur-NAc-L-Ala-D-isoGln-γ-L-Ala-decyl ester)

100 mg of the product obtained at (b) are dissolved in 2 ml of dimethylformamide. This solution is cooled to −15° C., and 23 μl of N-methylmorpholine added thereto. In addition, in a thermostatic cell at −15° C., is prepared a solution of 81 mg of benzy-O-benzylidene-4,6-N-acetyl muramic acid, prepared according to the method described by Ozawa T. and Jeanloz R. W. (J. Org. Chem., 1965, 30, 448), in 2 ml of dimethylformamide, then to this solution is added 20 μl of N-methylmorpholine, 23 μl of isobutyl chloroformate and, 5 minutes later, the previously obtained solution. After 4 hours, the temperature is allowed to rise again to 0° C. There is then added 0.18 ml of a 2.5 M KHCO3 solution and it is stirred again for 30 minutes. About 40 ml of water is then added to this solution and the resulting precipitate is drained, washed with 2.5 M KHCO3, then with water. 162 mg of the decyl ester of (benzyl-O-benzylidene-4,6-N-acetyl muramyl)-L-alanyl-D-isoglutaminyl-L-alanine are obtained. This precipitate is dissolved in about 10 ml of glacial acetic acid. 150 mg of 5% palladized carbon are added and the mixture is hydrogenated for 40 hours. The carbon is then filtered, the residue is evaporated, then taken up again in a water/acetic acid mixture and freeze-dried. 90 mg of the decyl ester of N-acetyl-muramyl-L-alanyl-D-isoglutaminyl-L-alanine are obtained. Its rotary power is $[\alpha]_D = +13.1$ (glacial acetic acid)

The elementary analysis is:

| for $C_{32}H_{57}N_5O_{12}$, 2 $CH_3COOH$ (823.92) | C | H | N |
|---|---|---|---|
| calculated: | 52.48 | 7.88 | 8.5 |
| found: | 52.30 | 7.77 | 8.97 |

(d) In the method which has just been described, the complete peptide chain is first synthesized, then fixed to the muramyl residue. Another method consists of starting from N-acetyl-muramyl-L-alanyl-D-isoglutamine, to fix the decyl ester derivative of L-alanyl prepared as has been described in (a).

To a mixture of N-acetyl-muramyl-L-alanyl-D-isoglutamine (0.5 m mole, 246.25 mg), hydroxybenzotriazole (0.5 mmole, 67.5 mg) and N-cyclohexyl-N′[β(N-methylmorpholino)ethyl]carbodiimide, p-toluene sulphonate (0.5 mmole, 211.8 mg) in 5 ml of dimethylformamide, are added, after an hour, the p-toluene sulphonate of the decyl ester of L-alanine (0.6 mmole, 241 mg) and N-methylmorpholine (0.6 mmole, 0.066 ml), in solution in 5 ml of dimethylmorpholine. After 48 hours of stirring at ambient temperature, the reaction mixture is diluted with an equal volume of 0.1 N acetic acid and the solution obtained is passed through a column of AG50 WX2, previously equilibrated in the mixture 0.1 N acetic acid-dimethylformamide (50/50).

After concentration of the fractions containing the product, the syrupy residue obtained was taken up again in a volume of 5 to 10 ml of dimethylformamide to which is added an equal volume of $2.10^{-3}$ M acetic acid. The solution was then passed through a column of AG1 X2, previously equilibrated in $2.10^{-3}$ M acetic acid-dimethylformamide (50/50).

After concentration of the fraction containing the product, the latter was obtained by lyophilization of its acetic solution.

A purification was finally carried out on a silica gel column in the solvent methanol-chloroform (1-3 v/v). 113 mg of the product were obtained, namely a yield of 32%. Its rotatory power was $[\alpha]_D^{25} = +20.9°$ (glacial acetic acid)

The elementary analysis is:

| for $C_{32}H_{57}N_5O_{12}$, $1H_2O$ (721.85) | C | H | N |
|---|---|---|---|
| calculated: | 53.19 | 8.23 | 9.66 |
| found: | 53.11 | 7.9 | 9.45 |

In the same way, by resorting to the same technique the following products were prepared:

—eicosyl ester of N-acetyl-muramyl-L-alanyl-D-isoglutamine-L-alanine whose rotatory power and elementary analysis were respectively $[\alpha]_D^{25} = +20°$ (glacial acetic acid) for $C_{42}H_{77}N_5O_{12}$, 0.75 $CH_3OH$, 0.25 $CHCl_3$

| | C | H | N |
|---|---|---|---|
| calculated: | 57.52 | 9.00 | 7.80 |
| found: | 57.53 | 8.74 | 7.79 |

—butyl ester of N-acetyl-muramyl-L-alanyl-D-isoglutamine-L-alanine whose rotatory power and elementary analysis were respectively $[\alpha]_D^{25} = +6.4°$ (methanol-water 1-3) for $C_{26}H_{45}N_5O_{12}$, 0.15 $CHCl_3$, 0.34 $H_2$)

| | C | H | N |
|---|---|---|---|
| calculated: | 48.79 | 7.17 | 10.88 |
| found: | 48.77 | 7.11 | 10.88 |

(2) Decylamide of N-acetyl-muramyl-L-alanyl-D-isoglutamine-L-alanine (a) Decylamide of the BOC-L-alanine 333 mg (1.16 mmoles) of BOC-Ala-OSu and 189 mg (1.2 mmoles) of decylamine were dissolved in 10 ml of dimethylformamide. The reaction mixture was allowed to stand for 1 hour at ordinary temperature, then concentrated to dryness. The product crystallized in needles when the ether added to the syrup obtained was evaporated. It was dried under vacuum in the presence of $P_2O_5$. 367 mg of product were obtained, namely a yield of 96%. Its physical constants are:

m.p. 60°-62° C.

$[\alpha]_D^{25} = -24°1$ (chloroform)

The elementary analysis is:

| for $C_{18}H_{36}N_2O_3$ | C | H | N |
|---|---|---|---|
| calculated: | 65.81 | 11.04 | 8.52 |
| found: | 65.67 | 10.8 | 8.28 |

(b) Hydrochloride of the decylamide of alanine 330 mg (1 mmole) of BOC-L-Ala-decylamide were treated with 4 ml of a normal solution of HCl in glacial acetic acid. After 30 minutes, the reaction mixture was concentrated to dryness and the product suspended in ether. 231 mg of product were obtained, namely a yield of 87.5%. The determination of the melting point shows a change in appearance at 95° C.

m.p. 157°-158° C.

$[\alpha]_D^{25} = +4.8°$ (methanol)

The elementary analysis is:

| for $C_{13}H_{28}N_2OCl$, 0.25 $H_2O$ | C | H | N |
|---|---|---|---|
| calculated: | 58.18 | 10.70 | 10.44 |
| found: | 58.24 | 10.53 | 10.26 |

(c) Decylamide of N-acetyl-muramyl-L-alanyl-D-isoglutaminyl-L-alanyl

The experimental method followed for the synthesis of this product is essentially the same as that used for the synthesis of the decyl ester of N-acetyl-muramyl-L-alanyl-D-isoglutaminyl-L-alanyl (second method of preparation (d)). The rotatory power and the elementary analysis of the product were:

$[\alpha]_D^{25} = +18.7°$ (glacial acetic acid)

| for $C_{32}H_{57}N_6O_{11}$, 0.5 $H_2O$ | C | H | N |
|---|---|---|---|
| calculated: | 53.99 | 8.35 | 11.80 |
| found: | 53.94 | 8.10 | 11.83 |

(3) n-butyl ester of N-acetyl-muramyl-L-alanyl-D-isoglutaminyl-L-alanine (a) p-toluene sulphonate of the n-butyl ester of L-alanine 891 mg (10 mmoles) of L-alanine and 2 g (10.5 mmoles) of p-toluene sulphonic acid are dissolved in 10 ml of n-butanol and 2 ml of benzene. The reaction mixture is heated under reflux (110°-120° C.) for 3 hours in a Soxhlet apparatus, the benzene being added regularly. The n-butanol and the benzene having been evaporated, the product is precipitated with ether, then crystallized in the methanol-ether mixture. 2.65 g of product are obtained, namely a yield of 83%. The characteristics of the product are:

m.p. 98°-99° C.

$[\alpha]_D^{20} = 0°$ C. (absolute methanol)

| for $C_{14}H_{23}NO_5S$ | C % | H % | N % |
|---|---|---|---|
| calculated: | 52.97 | 7.30 | 4.41 |
| found: | 52.58 | 7.05 | 4.23 |

(b) n-butyl ester of N-acetyl-muramyl-L-alanyl-D-isoglutaminyl-L-alanine

In solution in 8 ml of dimethylformamide, 493 mg (1 mmole) of N-acetyl-muramyl-L-alanyl-D-isoglutamine, 170 mg (1 mmole) of N-hydroxybenzotriazole, and 424 mg (1 mmole) of N-cyclohexyl-N'-[β(N-methyl-morpholino)ethyl]carbodiimide, p-toluene sulphonate, are allowed to stand for 1 hour at room temperature, then added to a solution in 7 ml of dimethylformamide of 224 mg (0.7 mmole) of the p-toluene sulphonate of N-butyl ester of L-alanine and of 0.077 ml (0.7 mmole) of N-methylmorpholine. After 4 days, the reaction mixture is concentrated to dryness, taken up again in an 0.1 M acetic acid solution and passed through a column of ion exchange resin marketed by the BIORAD Company under the name AG-50-W-X2 (8 to 10 ml). The interesting fractions are combined, freeze-dried, taken up again in a 2.10$^{-3}$ M acetic acid solution and passed through a column of ion exchange resin marketed by the BIORAD Company under the name AG-1-X2. The interesting fractions are combined and lyophilized. The product was then chromatographed on a silica gel column (8 g) in methanol-chloroform (1:4) mixture. After freeze-drying, 158 mg of product are obtained, namely a yield of 36.4%. The characteristics of the product are:

$[\alpha]_D^{20} = +6.4°$ (methanol-water, 1–3)

| for $C_{26}H_{45}N_5O_{12}$, 0.15 $CHCl_3$, 0.34 $H_2O$ | C % | H % | N % |
|---|---|---|---|
| calculated: | 48.79 | 7.17 | 10.88 |
| found: | 48.77 | 7.11 | 10.88 |

(4) Decyl ester of N-acetyl-muramyl-L-alanyl-D-isoglutaminyl-L-lysine (a) p-toluene sulphonate of decyl ester of N benzyloxycarbonyl-L-lysine 561 mg (2 mmoles) of N$^\epsilon$-benzyloxycarbonyl-L-lysine and 418 mg (2.2 mmoles) of p-toluene sulphonic acid are dissolved in 2 ml (10 mmoles) of decanol. The reaction mixture is heated under reflux (120° C.) for 5 hours in a Soxhlet apparatus, benzene being added regularly. The product was precipitated from this reaction mixture, then crystallized in the methanol-ether mixture. 941 mg of product were obtained, namely a yield of 77.5%. The characteristics of the product were:
m.p. 99°–100° C.
$[\alpha]_D^{20} = +1.8°$ (chloroform)

| for $C_{31}H_{48}N_2O_7S$ | C % | H % | N % |
|---|---|---|---|
| calculated: | 62.80 | 8.16 | 4.72 |
| found: | 62.88 | 8.25 | 4.79 |

(b) Decyl ester of N-acetyl-muramyl-L-alanyl-D-isoglutaminyl-N$^\epsilon$-benzyloxycarbonyl-L-lysine In solution in 5 ml of dimethylformamide, 492.5 mg (1 mmole) of N-acetyl-muramyl-L-alanyl-D-isoglutamine, 170 mg (1 mmole) of N-hydroxybenzotriazole and 424 mg (1 mmole) of N-cyclohexyl-N'[β-(N-methylmorpholino)ethyl]-carbodiimide, p-toluene sulphonate, are allowed to stand for one hour at room temperature, then added to a solution in 5 ml of dimethylformamide of 415 mg (0.7 mmole) of the p-toluene sulphonate of the decyl ester of N$^\epsilon$-benzyloxycarbonyl-L-lysine and of 0.077 ml (0.7 mmole) of N-methylmorpholine. After 48 hours at room temperature, the product was precipitated from the reaction mixture by the addition of 250 ml of iced water. It was then chromatographed on a silica gel column (20 g) in methanol-chloroform (1–5) mixture. 393 mg of product were obtained, namely a yield of 62.7%. The characteristics of the product were:
m.p. 174°–185° C.
$[\alpha]_D^{20} = +21°$ (glacial acetic acid)

| for $C_{43}H_{70}N_6O_{14}$ | C % | H % | N % |
|---|---|---|---|
| calculated: | 57.69 | 7.88 | 9.39 |
| found: | 56.8 | 7.79 | 9.14 |

(c) decyl ester of N-acetyl-muramyl-L-alanyl-D-isoglutaminyl-L-lysine 279 mg (0.31 mmole) of the decyl ester of the N-acetyl-muramyl-L-alanyl-D-isoglutaminyl-N$^\epsilon$-benzyloxycarbonyl-L-lysine, were hydrogenated, in solution in 25 ml of glacial acetic acid, in the presence of 200 mg of 5% palladium on carbon. After 2 hours, the catalyst was filtered and the product was obtained by freeze-drying. 255 mg of product were obtained, namely a yield of 100%, the characteristics of the product were:

$[\alpha]_D^{20} = +19°$ (glacial acetic acid)

| for $C_{37}H_{68}N_6O_{14}$, 1 $H_2O$ | C % | H % | N % |
|---|---|---|---|
| calculated: | 52.91 | 8.41 | 10.02 |
| found: | 52.78 | 7.99 | 10.02 |

(5) Pentadecyl ester of N-acetyl-muramyl-L-alanyl-D-isoglutaminyl-L-alanine (a) p-toluene sulphonate of the pentadecyl ester of L-alanine 400 mg (4.48 mmoles) of L-alanine, 937 mg (4.92 mmoles) of p-toluene sulphonic acid, and 4.4 g (19 mmoles) of pentadecanol were heated under reflux (120° C.) for 2 hours in a Soxhlet apparatus, in the presence of benzene. The product was precipitated with ether from the reaction mixture, then recrystallized in ether. 2.076 g of product were obtained, namely a yield of 98%. The characteristics of the product were:
m.p. 73° C.
$[\alpha]_D^{20} = 0°$ (chloroform)

| for $C_{25}H_{45}N_5S$ | C % | H % | N % |
|---|---|---|---|
| calculated: | 63.65 | 9.61 | 2.96 |
| found: | 63.27 | 9.26 | 3.25 |

(b) Pentadecyl ester of N-acetyl-muramyl-L-alanyl-D-isoglutaminyl-L-alanine

In solution in 5 ml of dimethylformamide, 492.5 mg (1 mmole) of N-acetyl-muramyl-L-alanyl-D-isoglutamine, 170 mg (1 mmole) of N-hydroxybenzotriazole and 424 mg (1 mmole) of N-cyclohexyl-N'[β-(N-methylmorpholino)ethyl]-carbodiimide, p-toluene sulphonate, were allowed to stand for one hour at room temperature, then added to a solution in 5 ml dimethylformamide of 330.2 mg (0.7 mmole) of the p-toluene sulphonate of the pentadecyl ester of L-alanine and 0.77 ml (0.7 mmole) of N-methylmorpholine. After 48 hours, the reaction mixture was evaporated to dryness and chromatographed on a silica gel column (40 g) in methanol-chloroform (1–4). The interesting fractions were combined, concentrated and the product was precipitated in methanol-water. 125 mg of this product were obtained, namely a yield of 23%. After passage over a new column of silica gel (MERCK—type A) in n-butanol-acetic acid-water mixture (4:1:5 upper phase), the product was recovered by freeze-drying. 68 mg of product were obtained whose characteristics were:

$[\alpha]_D^{20} = +19.5°$ (glacial acetic acid) for $C_{37}H_{67}N_5O_{12}$, 0.75 $CH_3COOH$, 0.5 $H_2O$

|  | C % | H % | N % |
|---|---|---|---|
| calculated: | 55.84 | 8.64 | 8.45 |
| found: | 55.60 | 8.10 | 8.47 |

(6) Benzyl ester of N-acetyl-muramyl-L-alanyl-D-isoglutaminyl-L-alanine

In solution in 8 ml of dimethylformamide, 493 mg (1 mmole) of N-acetyl-muramyl-L-alanyl-D-isoglutamine, 170 mg (1 mmole) of N-hydroxybenzotriazole and 424 mg (1 mmole) of N-cyclohexyl-N'[β-(N-methylmorpholino)ethyl]-carbodiimide, p-toluene sulphonate, were allowed to stand for an hour at room temperature, then added to a solution in 7 ml of dimethylformamide of 248 mg (0.7 mmole) of the p-toluene sulphonate of the benzyl ester of L-alanine and of 0.77 ml (0.7 mmole) of N-methylmorpholine. After 5 days, the reaction mixture was concentrated to dryness, taken up again in a 0.1 M acetic acid solution and passed through a column of AG-50-W-X2 resin. The interesting fractions were combined, freeze-dried, taken up in a $2.10^{-3}$ M acetic acid solution and passed through a column of AG-1-X2 resin. The fractions containing the product were combined, freeze-dried, then chromatographed over a column of silica gel (MERCK—type A) in the mixture n-butanol-acetic acid-water (150:5:25). The product was recovered by freeze-drying. 151 mg of product were obtained, namely a yield of 33%. The characteristics of the product were:

$[\alpha]_D^{20} = +5.2°$ ($H_2O$)

| for $C_{29}H_{43}N_5O_{12}$ | C % | H % | N % |
|---|---|---|---|
| calculated: | 53.28 | 6.63 | 10.71 |
| found: | 52.29 | 6.68 | 10.21 |

(7) Decyl ester of N-acetyl-muramyl-L-alanyl-D-isoglutamine (a) Hydrochloride of the decyl ester of D-isoglutamine A solution of 490 mg (2 mmoles) of BOC-D-isoglutamine(*) dissolved in 10 ml of methanol and 1 ml of water was adjusted to pH 7 with an aqueous solution of 20% $Cs_2CO_3$ (*)BOC=butyloxycarbonyl After evaporation to dryness and drying to the residue, 5 ml of dimethylformamide and 0.5 ml (2.2 mmoles) of 1-bromodecane were added. After 24 hours at ordinary temperature, the reaction mixture was concentrated to dryness, taken up in aqueous ethyl acetate and washed with water. The ethyl acetate phase was dried over $Na_2SO_4$, then evaporated. The product was crystallized in an ethyl acetate-petroleum ether mixture. 719 mg of product were obtained, namely a yield of 93%. The characteristics of the product were:
m.p. 106°-107° C.
$[\alpha]_D^{20} = +4.5°$ (chloroform)

| for $C_{20}H_{38}N_2O_5$ | C % | H % | N % |
|---|---|---|---|
| calculated: | 62.09 | 9.90 | 7.24 |
| found: | 62.35 | 9.96 | 7.26 |

The debutyloxycarbonylation, carried out by the action of a normal HCl solution in glacial acetic acid, enabled the product mentioned in the title to be obtained.

(b) Decyl ester of the hydrochloride of L-alanyl-D-isoglutamine 284 mg (1.5 mmole) of BOC-L-alanine are dissolved in 7 ml of dimethylformamide. To this solution cooled to 15° C. are successively added 0.165 ml (1.5 mmole) of N-methylmorpholine and 0.195 ml (1.5 mmole) of isobutyl chloroformate. After 3 minutes, a solution, cooled to 15° C. of 485 mg (1.5 mmole) of the hydrochloride of the decyl ester of the D-isoglutamine and 0.165 ml (1.5 mmole) of N-methylformamide, in 5 ml of dimethylformamide, was added. After 4 hours, the reaction mixture was brought to 0° C., and 2.5 ml of a 2.5 M $KHCO_3$ solution were added, then 50 ml of water. The product was extracted with ethyl acetate, and the extract was successively washed with 10% citric acid, with water, with a 1 M $NaHCO_3$ solution, and then with water.

The ethyl acetate phase was dried, then concentrated. The product was precipitated by the addition of petroleum ether. 632 mg of product were obtained, namely a yield of 92%. The characteristics of the product were:
m.p. 92°-93° C.
$[\alpha]_D^{20} = +2.5°$ (chloroform)

| for $C_{23}H_{43}N_3O_6$ | C % | H % | N % |
|---|---|---|---|
| calculated: | 60.36 | 9.47 | 9.18 |
| found: | 60.25 | 9.0 | 9.0 |

The debutyloxycarbonylation, carried out by the action of a normal HCl solution in glacial acetic acid, enabled the product mentioned in the heading to be obtained.

(c) Decyl ester of N-acetyl-muramyl-(1-α-benzyl-4,6-O-benzylidene)-L-alanyl-L-isoglutamine 471 mg (1 mmole) of (1-α-benzyl-4,6-benzylidene)-N-acetyl-muramic acid was dissolved in 5 ml of dimethylformamide. To this solution, cooled to −15° C., were successively added 0.11 ml (1 mmole) of N-methylmorpholine and 0.13 ml (1 mmole) of isobutyl chloroformate. After 3 minutes, a solution, cooled to −15° C., of 394 mg (1 mmole) of the hydrochloride of the decyl ester of L-alanyl-D-isoglutamine and 0.11 ml (1 mmole) of N-methylmorpholine, in 5 ml of dimethylfomamide, were added.

At the end of 4 hours, the reaction mixture was brought to 0° C., and 1.65 ml of a 2.5 M $KHCO_3$ solution was added and, after 30 minutes, 100 ml of water. The precipitated product was crystallized in methanol. 768 mg of product were obtained, namely a yield of 94.7%. The characteristics of the product were:
m.p. 235°-241° C. $[\alpha]_D^{20} = +83.7°$ (dimethylformamide)

(d) Decyl ester of N-acetyl-muramyl-L-alanyl-D-isoglutamine 400 mg (0.5 mmole) of decyl ester of N-acetyl-muramyl-(1-α-benzyl-4,6-O-benzylidene)-L-alanyl-D-isoglutamine were hydrogenated in glacial acetic acid, in the presence of 5% Pd on charcoal (400 mg).

After 48 hours, the catalyst was filtered, the acetic acid evaporated, and the product precipitated in methanol-ethyl acetate (twice). 200 mg of product were obtained. The characteristics of the product were:
m.p. 185°-190° C.

$[\alpha]_D^{20} = +38.7°$ (glacial acetic acid)

| for $C_{29}H_{52}N_4O_{11}$ | C % | H % | N % |
|---|---|---|---|
| calculated: | 55.04 | 8.28 | 8.692 |
| found: | 54.52 | 8.12 | 8.7 |

(8) α-methyl, γ-decyl N-acetyl-muramyl-L-alanyl-D-glutamic diester (a) Hydrochloride of the α-methyl, γ-decyl diester of D-glutamic acid 884.6 mg (2 mmoles) of the dicyclohexylamine salt of the α-methyl ester of BOC-D-glutamic acid were dissolved in 5 ml of water. This solution was supplemented with 3.26 ml of an aqueous solution of 20% $Cs_2CO_3$ (namely 2 mmoles), then concentrated to dryness and dried. The residue was taken up in 20 ml of dimethylformamide and 0.46 ml (2.2 mmoles) of bromodecane were added. After one night, the reaction mixture was concentrated and taken up again in aqueous ethyl acetate. The organic phase was washed with 10% citric acid, with water, with a molar solution of $NaHCO_3$, and then with water. It was dried over $MgSO_4$, filtered and concentrated. 791 mg of product were obtained, namely a yield of 98.5%.

The debutyloxycarbonylation was carried out by the action of a normal HCl solution in glacial acetic acid, enabling the product mentioned in the heading to be obtained. 987 mg of product were produced, namely a yield of 100%. The characteristics of the product were: m.p. 95°-97° C.

$[\alpha]_D^{20} = -13.3°$ (absolute methanol)

| for $C_{16}H_{32}NO_4Cl$ | C % | H % | N % |
|---|---|---|---|
| calculated: | 56.98 | 9.55 | 4.15 |
| found: | 56.49 | 9.34 | 4.25 |

(b) Hydrochloride of L-alanyl-D-glutamic α-methyl γ-decyl ester 593 mg (3.13 mmoles) of BOC-L-alanine were dissolved in 5 ml of dimethylformamide. To this solution, cooled to $-15°$ C., was successively added 0.35 ml (3.13 mmoles) of N-methylmorpholine and 0.4 ml (3.13 mmoles) of isobutyl chloroformate. After 3 minutes, a solution of 962 mg (2.85 mmoles) of hydrochloride of methyl α-ester, decyl γ-ester of D-glutamic acid and 0.3 ml (2.85 mmoles) of N-methylmorpholine in 5 ml of dimethylformamide, cooled to $-15°$ C., was added.

At the end of one night at $-15°$ C., the reaction mixture was brought to 0° C., then supplemented with 3 ml of a 2.5 M $KHCO_3$ solution. After 1 hour, 100 ml of water were added and the product was extracted with ethyl acetate, the organic phase was washed with 10% citric acid, with water, with a molar solution of $KHCO_3$, and then with water. It was dried over $MgSO_4$, filtered, concentrated to give a non-crystaline residue. 1.22 g of product were produced, namely a yield of 90.6%.

The debutyloxycarbonylation carried out by the action of a normal hydrochloric acid solution in glacial acetic acid enabled the production of the derivative given in the heading.

(c) α-methyl, γ-decyl N-acetyl-muramyl-(1-α-bemzyl-4,6-O-benzylidene)-L-alanyl-D-glutamic diester 1.216 g (2.8 mmoles) of 1-α-benzyl-4,6-O-benzylidene-N-acetyl-muramic acid were dissolved in 5 ml of dimethylformamide. To this solution, cooled to $-15°$ C., were successively added 0.31 ml (2.8 mmoles) of N-methylmorpholine and 0.37 ml (2.8 mmoles) of isobutyl chloroformate. After 3 minutes, a solution of 1.15 g (2.58 mmoles) of the hydrochloride of the α-methyl, γ-decyl L-alanyl-D-glutamic ester and 0.28 ml (2.58 mmoles) of N-methylformamide, in 5 ml of dimethylformamide, cooled to $-15°$ C., is added.

At the end of 4 hours, the reaction mixture was brought to 0° C. and supplemented with 2.8 ml of 2.5 M $KHCO_3$ solution. After 30 minutes, the product was precipitated by the addition of water. 1.87 g of product, namely a yield of 87.7% was obtained. The characteristics of the product were:
m.p. 207°-211° C.

$[\alpha]_D^{20} = +79°$ (dimethylformamide)

| for $C_{44}H_{63}N_3O_{12}$ | C % | H % | N % |
|---|---|---|---|
| calculated: | 63.98 | 7.69 | 5.09 |
| found: | 63.81 | 7.73 | 5.07 |

(d) α-methyl, γ-decyl N-acetyl-muramyl-L-alanyl-D-glutamic diester 1.6 g (2.3 mmoles) of the α-methyl, γ-decyl N-acetyl-muramyl-(1-α-benzyl-4,6-O-benzylidene)-L-alanyl-D-glutamic diester were hydrogenated in 100 ml of glacial acetic acid, for 41 hours, in the presence of 5% Pd on charcoal (1.9 g). After filtration of the catalyst, the acetic acid is evaporated and the residue is taken up in 4 ml of chloroform, chromatographed on a silica gel column (MERCK—type C) in methanol-chloroform-acetic acid mixture (7:1:0.2). The fractions containing the product were combined, concentrated, taken up with water and freeze-dried.

The product obtained is again purified on a silica gel column (silica 60–80 g) in the same mixture of solvents as previously, and finally freeze-dried. 929 mg of product were obtained whose characteristics were:

$[\alpha]_D^{20} = +26.3°$ (glacial acetic acid)

| for $C_{30}H_{53}N_3O_{12}$; 0.5 $CH_3COOH$, 1 $H_2O$ | C % | H % | N % |
|---|---|---|---|
| calculated: | 53.51 | 8.26 | 6.04 |
| found: | 54.14 | 7.96 | 6.14 |

(9) α-methyl, γ-n-butyl N-acetyl-muramyl-L-alanyl-D-glutamic diester (a) Hydrochloride of the α-methyl, γ-n-butyl D-glutamic diester 1.33 g (3 mmoles) of the dicyclohexylamine salt of the α-methyl ester of BOC-D-glutamic acid were dissolved in 5 ml of water. This solution was supplemented with 4.9 ml of an aqueous solutions of 20% of $Cs_2CO_3$ (namely 3 mmoles), then concentrated to dryness and dried. The residue was taken up in 50 ml of dimethylformamide, and 0.36 ml (3.3 mmoles) of bromobutane were added. After 20 hours, the reaction mixture was concentrated to dryness and taken up in aqueous ethyl acetate. The organic phase was washed with 10% citric acid, with water, with a molar solution of $KHCO_3$ and with water. It was dried over $MgSO_4$, filtered and concentrated. 884 mg of product were obtained, namely a yield of 93%.

The debutyloxycarbonylation, carried out by the action of a normal HCl solution in glacial acetic acid, led to the product given in the heading. 587 mg of product were obtained, namely a yeild of 83%. The characteristics of the product were:

m.p. 84°–88° C.
$[\alpha]_D^{20} = -20°$ (absolute methanol)

| for C$_{10}$H$_{20}$NO$_4$Cl | C % | H % | N % |
|---|---|---|---|
| calculated: | 47.34 | 7.95 | 5.52 |
| found: | 47.39 | 7.49 | 5.15 |

(b) Hydrochloride of the α-methyl, γ-n-butyl L-alanyl-D-glutamic diester 473 mg (2.5 mmoles) of BOC-L-alanine were dissolved in 5 ml dimethylformamide. To this solution, cooled to −15° C., were successively added 0.28 ml (2.5 mmoles) of N-methylmorpholine and 0.33 ml (2.5 mmoles) of isobutyl chloroformate. After 3 minutes, a solution of 558 mg (2.2 mmoles) of hydrochloride of the α-methyl, γ-n-butyl diester of D-glutamic acid and 0.24 ml (2.2 mmoles) of N-methylmorpholine, in 5 ml of dimethylformamide, cooled to −15° C., was added.

At the end of one night at −15° C., the reaction mixture was brought to 0° C., then supplemented with 3 ml of a 2.5 M KHCO$_3$ solution. After one hour, 100 ml of water were added and the product was extracted with ethyl acetate. The organic phase was washed with 10% citric acid, and with water, with a molar solution of KHCO$_3$, then with water. It was dried over MgSO$_4$ and filtered, concentrated to give a non-crystalline residue. 804 mg of product, namely a yield of 94% was obtained.

The debutyloxycarbonylation, carried out by the action of normal hydrochloric acid solution in glacial acetic acid enabled the obtaining of the derivative given in the heading.

(c) α-methyl, γ-n-butyl N-acetyl-muramyl-(1-α-bemzyl-4,6-O-benzylidene)-L-alanyl-D-glutamic diester 1,037 g (2.2 mmoles) of 1-α-benzyl-4,6-O-benzylidene-N-acetyl-muramic acid were dissolved in 5 ml of dimethylformamide. To this solution, cooled to −15° C., were successively added 0.24 ml (2.2 mmoles) of N-methylmorpholine and 0.29 ml (2.2 mmoles) of isobutyl chloroformate. After 3 minutes, a solution of 700 mg (2.1 mmoles) of the hydrochloride of the α-methyl, γ-n-butyl L-alanyl-D-glutamic diester and 0.24 ml (2.1 mmoles) of N-methylmorpholine in 5 ml of dimethylformamide was cooled to −15° C. and added.

At the end of 4 hours, the reaction mixture was brought to 0° C. and supplemented with 2.5 ml of a 2.5 M KHCO$_3$ solution. After 30 minutes, the product was precipitated by the addition of water. 1.365 g of product, namely a yield of 89.3% was obtained. The characteristics of the product were:

m.p. 195°–203° C.
$[\alpha]_D^{20} = +92.3°$ (dimethylformamide

| for C$_{38}$H$_{51}$N$_3$O$_{12}$ | C % | H % | N % |
|---|---|---|---|
| calculated: | 61.52 | 6.93 | 5.66 |
| found: | 61.47 | 7.02 | 5.41 |

(d) α-methyl, γ-n-butyl N-acetyl-muramyl-L-alanyl-D-glutamic diester 1.34 g (1.8 mmoles) of the α-methyl, γ-n-butyl N-acetyl-muramyl-(1-α-benzyl-4,6-O-benzylidene)-L-alanyl-D-glutamic diester were hydrogenated in 50 ml of glacial acetic acid, for 40 hours, in the presence of 5% Pd on charcoal (1.35 g). After filtration of the catalyst and evaporation of the acetic acid, the product was chromatographed on a silica gel column (silica 60–80 g) in chloroform-methanol-acetic acetic acid mixture (6:1:0.2). The fractions containing the product were combined, concentrated, and taken up in water, then freezed-dried. 658.4 mg of product, namely a yield of 66% was obtained. The characteristics of the product were:

$[\alpha]_D^{20} = +30.8°$ (glacial acetic acid)

| for C$_{24}$H$_{41}$N$_3$O$_{12}$; 0.3 CH$_3$COOH, 1 H$_2$O | C % | H % | N % |
|---|---|---|---|
| calculated: | 49.44 | 7.12 | 7.03 |
| found: | 49.01 | 7.03 | 7.12 |

(10) N-acetyl-muramyl-L-alanyl-D-isoglutaminyl-L-alanylglyceryl-mycolate (a) tosyl-glyceryl-mycolate To 3.5 g of glycerol monomycolate, in solution in 25 ml of dried pyridine, were added 6 portions of 126 mg of tosyl chloride. At the end of 72 hours, the reaction mixture was concentrated and the residue was tritrated in toluene. The latter was collected and concentrated after filtration. The product was purified by chromatography on a silica gel column (silica 60) in batches of 1.8 g each, in the chloroform-ether mixture (95–5). 1.719 g of product were obtained, namely a yield of 46%.

(b) L-alanyl-glyceryl-mycolate hydrochloride 1.45 g (1 mmole) of tosyl-glyceryl-mycolate dissolved in 20 ml of dry benzene were added to 250 mg of the potassium salt of BOC-L-alanine and to 140 mg of 18-crown-6 in solution in 15 ml of dry benzene. The reaction mixture was heated under reflux for 6 hours under strictly anhydrous conditions, then, after cooling, it was filtered and concentrated to dryness. The product was chromatographed on a silica gel column (silica 60) in the benzene-ether mixture (65–35). 958 mg of product were obtained, namely a yield of 65%.

The debutyloxycarbonylation by the action of a normal HCl solution in glacial acetic acid enabled the production of 970 mg of product given in the heading.

(c) N-acetyl-muramyl-L-alanyl-D-isoglutaminyl-L-alanyl-glyceryl-mycolate

In solution in 15 ml of dimethylformamide, 352 mg of N N-acetyl-muramyl-L-alanyl-D-isoglutamine, 121.5 mg of N-hydroxybenzotriazole and 303 mg of N-cyclohexyl-N'[β-(N-methylmorpholino)ethyl]-carbodiimide, p-toluene sulphonate, were allowed to stand for 1 hour at room temperature and then added to a solution in 10 ml of dry benzene of 970 mg of hydrochloride of L-alanyl-glyceryl-mycolate and of 0.075 ml of N-methylmorpholine.

After 28 hours at room temperature, the reaction mixture was brought to dryness. The residue was taken up in a benzene-methanol (50-1) mixture, and filtered over silica to remove all traces of dimethylformamide. The concentrated eluate was purified by the passage over a silica gel column in benzene-methanol (5-1) mixture. The interesting fractions were combined, concentrated, taken up in hot acetic acid (60° C.) and freeze-dried. 684.6 mg of product were obtained, namely a yield of 57%. The characteristics of the product were:

$[\alpha]_D^{20} = +12°$ (benzene)

| for C$_{109}$H$_{205}$O$_{16}$N$_5$; 1.5 CH$_3$COOH | C % | H % | N % |
|---|---|---|---|
| calculated: | 69.63 | 11.01 | 3.62 |

-continued

| for $C_{109}H_{205}O_{16}N_5$; 1.5 $CH_3COOH$ | | |
|---|---|---|
| C % | H % | N % |
| found: 69.90 | 10.91 | 3.34 |

METHOD OF PREPARATION OF LIPOSOMES

10 μmoles (7.3 mg) of DL-dipalmitoyl-α-phosphatidyl-choline (PM 734, grade I, approximately 99%, marketed by SIGMA) and 10 μmoles (3.9 mg) of cholesterol (PM 366, 6, 99+%, SIGMA) were dissolved in about 5 ml of chloroform (pure grade) in a round bottom 10 ml flask.

The lipophile adjuvants, in the proportion of 1.0 mg, were introduced with a chloroform phase.

The solution was evaporated in a rotary evaporator under vacuum at a temperature below 30° C. so as to obtain a fine film of lecithin+ cholesterol on the inner wall of the flask.

5 ml of a buffer solution of 0.013 M sodium phosphate, pH 7.0, containing 9°/oo of NaCl are brought to 55° C. The water-soluble adjuvants are introduced into this solution. In addition, the flask containing the above lipid film is also heated to 55° C.

The buffer solution is slowly poured into the flask keeping the temperature at 55° C. The contents are then subjected to gentle stirring at 55° C. so as to obtain a suspension of liposomes containing the envisaged adjuvant. It is left to stand for about 1 hour.

The preparation is then subjected to sonication at 0° C. under a nitrogen or argon atmosphere for 30 seconds (0.3 kW).

When the adjuvants are water-soluble, the suspension is also centrifuged at 100,000 g, the culot is taken up with the phosphate buffer-NaCl. The operation is repeated six times. The culot finally obtained is taken up with a phosphate buffer-NaCl solution, to the selected volume.

PHARMACOLOGICAL PROPERTIES

The tests whose results are given below relate to various products corresponding to the general formula (1). For convenience, for these products, the group N-acetyl-muramyl-L-alanyl-D-isoglutaminyl is denoted by MDP, in the same way as the group N-acetyl-muramyl-L-alanyl-D-glutamyl is denoted by MDPA.

(1) Toxicity

The toxicity of the products according to the invention was investigated by parenteral administration in mice. It was observed that the toxic doses were of an order of magnitude very much higher than that of the doses at which these products manifest their activity. Thus the lethal dose 50 of the products according to the invention tested was higher than 5 mg/kg of animal in the adrenalectomised mouse, whose sensitivity to endotoxins is well-known.

The tested products were notably:
—MDP decyl-ester
—MDP-L-Ala-decyl-amide
—MDP-L-Ala-eicosyl-ester
—MDP-L-Ala-glyceryl-mycolate
—MDP-L-Ala-benzyl-ester
—MDP-L-Lys-decyl-ester It is possible to demonstrate the very favorable properties of the products according to the invention, notably by resorting to the tests described below.

(2) Limulus test

To show the absence of activity of the endotoxic type, products according to the invention were subjected to the Limulus test. For this purpose, 0.1 ml of the Limulus amoebocyte lysate preparation (marketed by the MALLINCKRODT Company, at St. LOUIS, U.S.A.) was mixed with an equal volume of the tested product at various concentrations in solution in apyrogenic distilled water. The vessels used were also made apyrogenic by dry heating in the oven, at 180° C., for 2 hours.

After incubating the mixture for 20 minutes at 37° C. in tubes, the formation of gel characteristics of the presence of endotoxin was estimated.

A test is positive when the presence of a firm gel is observed which remains adherent to the bottom of the tube when the latter is inverted (technique described by Elin R. J. and Wolff S. M., J. Infect. Dis., 1973, 128: 349). the results of these tests are as follows:

| | |
|---|---|
| MDP—L—Ala—butyl—ester | 100 μg/ml |
| MDP—L—Ala—decyl—ester | 100 μg/ml |
| MDP—L—Ala—decyl—amide | 100 μg/ml |
| MDP—L—Ala—eicosyl—ester | 10 μg/ml |
| MDP—L—Ala—glycosyl—mycolate | 100 μg/ml |

Under the same conditions, the LPS extract of *Escherichia coli* by way of comparison is positive at 0.01 μg/ml.

These results show, taking into account the effective anti-infectious doses, that the properties demonstrated in the following tests could not arise from endotoxic contamination.

(3) Adjuvant character in the aqueous phase and in emulsion (a) In the aqueous phase Groups of 8 Swiss mice aged two months received, by sub-cutaneous injection (SC), 0.5 mg of antigen constituted by bovine serum albumin (BSA) with 0.1 mg or without the tested substance in an isotonic saline solution. This high dose of antigen, because it is situated at the limit of the paralyzing dose with respect to the immunitary response, results, for this reason, in a weak or zero response to the antigen only in the controls: It constitutes therefore a severe criterien to establish the activity of an adjuvant substance. Thirty days later, the mice received, by the same administrative route, a booster containing 0.1 mg of the same antigen.

The antibody level was determined, six days after the booster, by passive hemagglutination using sheep's red blood corpuscles treated with formalin and covered with the antigen studied according to the method described by A. A. HIRATA and M. W. BRANDISS (J. Immunol., 100, 641-648, 1968).

The antibody titer, represented by the maximum serum dilution agglutinating a given amount of sheep corpuscles, reaches a maximum at the 36th day and is established in the following manner:

| | $Log_2$ hemagglutinating titer |
|---|---|
| Controls | 3.15 ± 1.72 |
| MDP | 8.24 ± 1.27 |
| MDP—decyl—ester | 8.64 ± 1.31 |
| MDP—L—Ala—butyl—ester | 10.31 ± 0.49 |
| MDP—L—Ala—decyl—ester | 6.23 ± 1.23 |
| MDP—L—Ala—decyl—amide | 8.64 ± 0.95 |
| MDP—L—Ala—penta—decyl—ester | 8.39 ± 0.89 |
| MDP—L—Ala—cicosyl—ester | 7.11 ± 2.03 |
| MDP—L—Ala—glyceryl—mycolate | 7.47 ± 1.17 |
| MDP—L—Ala—benzyl—ester | 7.47 ± 0.89 |

| | Log$_2$ hemagglutinating titer |
|---|---|
| MDP—L—Lys—decyl—ester | 9.64 ± 0.70 |

The titers are expressed in base 2 logarithms. It is seen that all the compounds permitted the level of the humoral response to be considerably increased (at least 8 times and up to more than 100 times).

(b) In emulsion

The tests were carried out on batches of 6 male Hartley guinea pigs of 350 g. The administration was done by intradermal injection into the plantar pad of each of the rear paws. Ovalbumin (constituting the antigen) in the amount of 1 mg is prepared in 0.1 ml of an emulsion of saline isotonic solution, in any oily phase constituted either by the Freund imcomplete adjuvant (FIA), or by the complete adjuvant (FCA) formed by the FIA to which is added 0.1 mg of whole *Mycobacterium smegmatis* cells. The compound according to the invention was administered in the amount of 0.05 mg added in the emulsion containing the FIA.

Eighteen days after this immunization, possible delayed hypersensitivity reactions to the antigen were sought by injecting by the intradermal route 0.01 mg of ovalbumin in the side of the animals, and 48 hours later, the reaction of the point of injection was observed. The diameter in millimeters of the reaction thus caused was measured.

Twenty-one days after the injection, the animals were bled. On the collected serum, the content of specific antibodies of the ovalbumin was measured by precipitation of the antibody-antigen complex in the equivalence zone. The amount of protein nitrogen contained in the precipitate was estimated by the Folin method. The average values of the contents of antibodies are indicated in the table of results. These values express the amount, in micrograms, of nitrogen precipitatable by the antigen, per milliliter of the serum.

The results of these tests are as follows.

These results show that the tested products caused, to various degrees, an increase in the level of the antibodies formed.

The administration of the product also generates a delayed type of hypersensitization in the treated subject with respect to the antigen, which hypersensitization is revealed by the cutaneous test.

(4) Anti-infectious activity with respect to Klebsiella

The testing procedure is described in the article CHEDID L. et col., Proc. Natl. Acad. Sci. U.S.A., 74:2089.

In this way there was previously established an experimental method permitting the anti-infectious character of the product to be demonstrated. It was shown that a dose of about $10^4$ *Klebsiella pneumoniae*, injected by the intramuscular route in mice, results in the gradual death of a considerable part, if not all, of the animals in the week following the inoculation. After 8 days, the survival of the animals was definitely achieved.

The survival of groups of inoculated mice under the above conditions and treated by means of the products according to the invention was followed.

For these tests, hybrid mice (C57B1/6×AKR) F1 bred at the PASTEUR INSTITUTE, from strains derived from the CNRS breeding station at ORLEANS, were used.

The infection by *Klebsiella pneumoniae*, a strain of the capsular 2, biotype d type, was done from a culture of 16 hours in a medium for pneumococci (No. 53515, PASTEUR INSTITUTE). The infecting dose was $2.10^4$ Klebsiella; it was administered by the intramuscular route.

The administration of the tested product was carried out by the intravenous route in 0.2 ml of apyrogenic physiological solution, the controls receiving the solution alone. It was carried out 24 hours before the inoculation.

The results of these tests are reported in the following table. The percentage protection indicated is a difference of the percentages of survivors of the treated group with respect to the control group.

| | HSR | Log$_2$ of the hemagglutinating titer |
|---|---|---|
| Control (AIF) | 0 | 10.29 ± 0.75 |
| AIF + 50 μg MDP | 14 ± 4 | 12.58 ± 1.02 |
| AIF + 50 μg MDP—L—Ala—butyl—ester | 18 ± 2 | 13.31 ± 0.52 |
| AIF + 50 μg MDP—L—Ala—decyl—ester | 17 ± 2.5 | 10.81 ± 1.47° |
| AIF + 50 μg MDP—L—Ala—decyl—ester | 5 | 12.31 ± 0.82 |
| AIF + 50 μg MDP—L—Ala—penta—decyl—ester | 5 | 10.97 ± 1.04 |
| AIF + 50 μg MDP—L—Ala—eicosyl—ester | 6 ± 4 | 11.25 ± 1.14+ |
| AIF + 50 μg MDP—L—Ala—glyceryl—mycolate | 21 ± 3 | 12.77 ± 0.83 |
| AIF + 50 μg MDP—L—Ala—benzyl—ester | 12.5 ± 3.5 | 12.31 ± 0.82 |
| AIF + 50 μg MDP—L—Ala—decyl—ester | 13 ± 2 | 13.4 ± 0.55 |

| i.v. Treatment 24h before $2 \times 10^4$ bacteria i.m. | Dose per mouse | Number of treated mice | Number of survivors at day | | | % of protection |
|---|---|---|---|---|---|---|
| | | | 3 | 5 | 8 | |
| Controls | — | 24 | 8 | 3 | 3 | |
| MDP—decyl—ester | 10 | 8 | 1 | 0 | 0 | |
| | 100 | 24 | 24 | 21 | 21 | 75 |
| Controls | — | 24 | 13 | 5 | 4 | |
| MDP—L—Ala—butyl—ester | 100 | 24 | 23 | 18 | 17 | 54 |
| Controls | — | 32 | 13 | 9 | 8 | |
| MDP—L—Ala—decyl—ester | 100 | 32 | 30 | 22 | 22 | 44 |
| Controls | — | 24 | 13 | 5 | 4 | |

-continued

| i.v. Treatment 24h before 2 × 10⁴ bacteria i.m. | Dose per mouse | Number of treated mice | Number of survivors at day 3 | 5 | 8 | % of protection |
|---|---|---|---|---|---|---|
| MDP—L—Ala—decyl—amide | 100 | 24 | 21 | 17 | 16 | 50 |
| Controls | — | 24 | 8 | 3 | 3 | |
| MDP—L—Ala—penta—decyl—ester | 100 | 24 | 24 | 16 | 15 | 50 |
| Controls | — | 24 | 12 | 4 | 3 | |
| MDP—L—Ala—eicosyl—ester | 10 | 24 | 18 | 14 | 14 | 46 |
| | 100 | 24 | 23 | 23 | 20 | 70 |
| Controls | — | 24 | 7 | 4 | 4 | |
| MDP—L—Ala—glyceryl—mycolate | 10 | 8 | 5 | 4 | 4 | 33 |
| | 100 | 24 | 23 | 23 | 23 | 79 |
| Controls | — | 24 | 8 | 3 | 3 | |
| MDP—L—Ala—benzyl—ester | 100 | 24 | 24 | 14 | 14 | 46 |
| Controls | — | 24 | 8 | 3 | 3 | |
| MDP—L—Lys—decyl—ester | 100 | 24 | 22 | 20 | 20 | 71 |
| Controls | — | 16 | 7 | 3 | 3 | |
| MDPA(butyl—ester)OCH₃ | 100 | 16 | 12 | 11 | 9 | 38 |
| Controls | — | 16 | 7 | 3 | 3 | |
| MDPA(decyl—ester)OCH₃ | 100 | 16 | 13 | 11 | 10 | 44 |

The results show significantly increased protection in applying the Student t test, for the animals which had received the products according to the invention with respect to the control animals.

(5) Anti-infectious activity with respect to Listeria

Under similar conditions to those tests No. (4), the influence of the administration of Mur-NAc-L-Ala-D-isoGln-γ-L-Ala-decyl-ester was determined on the mortality of mice in which a dose of *Listeria monocytogenes* was inoculated, known for causing typically a cellular type infection.

As previously, the action of the product according to the invention was compared with that of BCG whose anti-infectious properties are well-known in this field. There were also determined, still by way of comparison, the action of LPS, *Corynebacterium granulosum*, and Mur-NAc-L-Ala-D-isoGln (MDP).

The treatment of the mice and the inoculation was carried out by the intravenous route. The injected products were in solution or suspension in 0.2 ml of apyrogenic physiological solution. The controls only received the solution.

The dose of Listeria administration was, in all tests, 1.10³ units.

The tests whose results are given below were carried out by varying the doses of tested products and the time intervals separating the treatment from the inoculation of the *Listeria monocytogenes* (either 1, or 7 days). The number of surviving mice at the 5th and 10th day following the inoculation, was watched and the percentage protection as for the preceding tests was determined.

| Intravenous treatment | Dose per mouse µg | Number of days before infection | Number of mice | Number of surviving animals at day 5 | 10 | % of protection |
|---|---|---|---|---|---|---|
| Controls | | | 40 | 1 | 1 | |
| LPS | 0,3 | 1 | 32 | 18 | 9 | 26 |
| Controls | | | 8 | 0 | | |
| BCG | 100 | 1 | 8 | 1 | 0 | |
| BCG | 100 | 7 | 8 | 6 | 6 | 75 |
| Controls | | | 24 | 3 | 2 | |
| C. granulosum | 300 | 1 | 8 | 0 | | |
| C. granulosum | 300 | 7 | 24 | 12 | 11 | 38 |
| Controls | | | 40 | 9 | 4 | |
| MDP | 100 | 1 | 32 | 6 | 2 | |
| MDP | 1000 | 1 | 8 | 2 | 1 | |
| MDP | 1000 | 4 | 8 | 2 | 2 | |
| MDP | 100 | 7 | 16 | 3 | 1 | |
| Controls | — | — | 24 | 11 | 2 | |
| Mur—NAc—L—Ala—D—isoGln—γ—L—Ala— | 10 | 1 | 8 | 7 | 5 | 50 |
| Mur—NAc—L—Ala—D—isodecyl—ester | 100 | 1 | 24 | 19 | 11 | 38 |
| Mur—NAc—L—Ala—D—isodecyl—ester | 300 | 1 | 16 | 11 | 5 | 23 |

These results show, on the one hand, the absence of practically all protection by means of MDP under the conditions of the experiment and, on the contrary, very significant protection in the case of the products according to the invention, and this even at a very low dose of product (10 µg).

(6) Tests of the liposome forms

Pharmacological tests similar to the preceding ones were reproduced with MDP, MDP-L-Ala-eicosyl-ester and MDP-L-Ala-glyceryl-mycolate comparing the effects of administration in liposome form with those obtained for products in solution and with liposomes without muramyl-peptide.

The liposomes were prepared in the manner described above.

(a) Toxicity in the adrenalectomized mouse

The products, the doses administered and their effect on the mortality of groups of six mice are indicated below.

| | Number of dead mice |
|---|---|
| Bare liposomes 1/20 ml | 0/6 |
| MDP 100 μg | 0/6 |
| MDP liposomes 1,3 μg (= 1/20 ml) | 0/6 |
| MDP—L—Ala—eicosyl—ester 100 μg | 0/6 |
| MDP—L—Ala—eicosyl—ester liposomes 100 μg (= 1/20 ml) | 0/6 |
| MDP—L—Ala—glyceryl—mycolate 100 μg | 0/6 |
| MDP—L—Ala—glyceryl—mycolate liposomes 100 μg (= 1/20 ml) | 0/6 |

It was observed, as previously, that the lethal dose 50 is situated well beyond 5 mg/kg, whether the product was administered in solution or in liposome form.

(b) Adjuvant character

The series of tests was carried out on mice under the same conditions as indicated in (3)(a), using BSA as antigen.

The results of these tests are the following.

| | $Log_2$ of the hemag-glutinating titer |
|---|---|
| Controls | 1.64 |
| Bare liposomes | 1.64 |
| MDP 100 μg | 8.21 ± 0.53 |
| 10 μg | 6.89 ± 2.05 |
| MDP—L—Ala—eicosyl—ester 10 μg | 3.64 ± 1.15 |
| MDP—L—Ala—glyceryl—mycolate 10 μg | 2.07 ± 1.13 |
| MDP—L—Ala—eicosyl—ester liposomes (10 μg of the MDP derivative) | 2.78 ± 1.35 |
| MDP—L—Ala—glyceryl—mycolate liposomes (10 μg of the MDP derivative) | 2.07 ± 1.13 |

A second series of tests was carried out on Wistar rats, under the following conditions.

The antigen was ovalbumin injected by the subcutaneous route in male Wistar rats in a volume of 0.5 ml at the dose of 0.5 mg. The adjuvant preparations were injected simultaneously, at the dose indicated. At day 20, the animals received a booster of 0.5 mg of antigen alone by the same route. The serums were drawn and tested under the same conditions as in the mouse with the appropriate antigen.

The results obtained were:

| | $Log_2$ of the hemagglutinating titer |
|---|---|
| Controls | 5.14 ± 1.38 |
| Bare liposomes | 5.31 ± 2.8 |
| MDP 200 μg | 4.97 ± 0.82 |
| MDP liposomes 2.5 μg | 7.64 ± 1.24 |
| MDP—L—Ala—glyceryl—mycolate (200 μg) | 7.64 ± 1.90 |
| MDP—L—Ala—glyceryl—mycolate liposomes | 6.47 ± 2.32 |
| Eicosyl—ester liposomes (200 μg) | 8.64 ± 1.26 |

A third series of tests was carried out on guinea pigs. The conditions of these tests are as follows.

The antigen was ovalbumin injected in aqueous solution in the foot pad of Hartley male guinea pigs at a volume of 0.1 ml in each rear paw, at the dose of 1 mg per guinea pig. The adjuvant preparations were injected simultaneously at the indicated doses. After three weeks, the animals received by the dermal route, in a volume of 0.1 ml, 0.025 mg of antigen. The diameter of the cutaneous reactions was measured after 48 hours. The animals were bled and the titers measured.

The results obtained were the following:

| | HSR | $Log_2$ of the hemag-glutinating titer |
|---|---|---|
| Controls | 0 | 6.64 ± 0.82 |
| MDP 200 μg | 0 | 9.19 ± 1.37 |
| MDP liposomes 2.5 μg | 4(5)*0(6) | 7.37 ± 1.19 |
| MDP—L—Ala—eicosyl—ester 200 μg | 0 | 7.33 ± 1.51 |
| MDP—L—Ala—eicosyl—ester liposomes 200 μg | 8(3)0(3) | 9.64 ± 0.63 |
| MDP—L—Ala—glyceryl—mycolate | 0 | 8.64 ± 1.83 |
| MDP—L—Ala—glyceryl—mycolate liposomes 200 μg | 9 ± 2 | 9.64 ± 1.55 |

*between parentheses, number of animals showing the reaction indicated.

The whole of these results shows that the administration in the form of liposomes preserves generally the adjuvant activity of the products and can even sometimes improve it. The most sensitive effect is manifested at the level of the delayed hypersensitivity of phenomena.

(c) Anti-Klebsiella activity

Under the previously described conditions, with the exception of the infection produced by the intravenous injection of $1.5.10^3$ Klebsiella, the tests are renewed to determine the anti-infectious action. The administrations in the form of solution and of liposome were prepared.

The results regrouped in the following table show, for an equal content of the tested compound, an appreciable improvement in the effectiveness for the liposome form with respect to the solution.

| i.v. Treatment at D − 1 | Number of mice | Number of survivors at D + 3 | D + 5 | D + 8 | % of protection |
|---|---|---|---|---|---|
| Controls | 24 | 8 | 6 | 6 | — |
| Bare liposomes 1/20000 ml | 16 | 3 | 3 | 2 | 0 |
| 1/2000 ml | 16 | 5 | 4 | 4 | 0 |
| 1/200 ml | 24 | 10 | 7 | 6 | 0 |
| MDP 1 μg | 16 | 5 | 3 | 2 | 0 |
| 10 μg | 16 | 9 | 5 | 5 | 6 |
| 100 μg | 24 | 21 | 15 | 15 | 38 |
| Liposomes MDP 0,001 μg | 16 | 0 | 0 | 0 | 0 |
| 0,01 μg | 16 | 1 | 1 | 1 | 0 |
| 0,13 μg = 1/200 ml | 16 | 11 | 10 | 10 | 38 |
| MDP—L—Ala—eicosyl—ester 1 μg | 8 | 4 | 4 | 4 | 25 |

| i.v. Treatment at D − 1 | Number of mice | Number of survivors at D + 3 | D + 5 | D + 8 | % of protection |
|---|---|---|---|---|---|
| 10 μg | 16 | 13 | 9 | 9 | 31 |
| 100 μg | 16 | 14 | 14 | 14 | 63 |
| Liposomes MDP—L—Ala—eicosyl—ester | | | | | |
| 0,1 μg | 24 | 9 | 8 | 8 | 8 |
| 1 μg | 24 | 10 | 8 | 8 | 8 |
| 10 μg = 1/200 ml | 24 | 19 | 19 | 19 | 54 |
| MDP—L—Ala—glyceryl—mycolate 1 μg | 8 | 2 | 2 | 2 | 0 |
| 10 μg | 16 | 9 | 8 | 8 | 25 |
| 100 μg | 8 | 8 | 7 | 7 | 63 |
| Liposomes MDP—L—Ala—glyceryl— | | | | | |
| mycolate 0,1 μg | 24 | 5 | 4 | 3 | 0 |
| 1 μg | 24 | 10 | 10 | 10 | 17 |
| 10 μg | 24 | 15 | 15 | 14 | 33 |

(d) Anti-Listeria Activity

The tests were carried out under the conditions of (5), using a dose of *Listeria monocytogen*, known to cause typically a cellular type infection.

The treatment of the mice and the inoculation were carried out by the intravenous route. The products were injected in the liposome form at the indicated doses. The controls only received isotonic solution.

The dose of Listeria administered was, in all the tests, $1.10^3$ cells.

The tests whose results are given below were carried out by varying the interval of time separating the treatment of inoculation from the *Listeria monocytogenes* (either 1, either 4, or 8 days). The number of surviving mice at the 5th and at the 10th day following inoculation was followed, and the percentage protection determined as for the preceding tests.

| Time | i.v. Treatment Product | Dose μg | Number of mice | Number of survivors D + 5 | D + 10 | % of protection |
|---|---|---|---|---|---|---|
| D − 1 | Controls | — | 16 | 6 | 2 | — |
| | Bare liposomes (1/20 ml) | — | 16 | 6 | 3 | — |
| | Liposomes MDP | 1,3 | 16 | 8 | 7 | 25 |
| | MDP—L—Ala—eicosyl—ester | 100 | 16 | 3 | 0 | 0 |
| | Liposomes MDP—L—Ala—eicosyl—ester | 100 | 16 | 2 | 0 | 0 |
| | MDP—L—Ala—glyceryl—mycolate | 100 | 8 | 3 | 2 | 0 |
| | Liposomes MDP—L—Ala—glyceryl—mycolate | 100 | 16 | 8 | 6 | 19 |
| D − 4 | Controls | — | 16 | 6 | 2 | — |
| | Bare liposomes (1/20 ml) | — | 16 | 8 | 4 | — |
| | Liposomes MDP | 1,3 | 16 | 14 | 5 | 6 |
| | MDP—L—Ala—eicosyl—ester | 100 | 16 | 4 | 4 | 0 |
| | Liposomes MDP—L—Ala—eicosyl—ester | 100 | 16 | 9 | 2 | 0 |
| | MDP—L—Ala—glyceryl—mycolate | 100 | 8 | 1 | 0 | 0 |
| | Liposomes MDP—L—Ala—glyceryl—mycolate | 100 | 16 | 14 | 9 | 31 |
| D − 8 | Controls | — | 16 | 5 | 2 | — |
| | Bare liposomes (1/20 ml) | — | 16 | 4 | 3 | — |
| | Liposomes MDP | 1,3 | 16 | 6 | 3 | 0 |
| | MDP—L—Ala—eicosyl—ester | 100 | 8 | 2 | 2 | 0 |
| | Liposomes MDP—L—Ala—eicosyl—ester | 100 | 16 | 12 | 7 | 25 |
| | MDP—L—Ala—glyceryl—mycolate | 100 | 8 | 1 | 0 | 0 |
| | Liposomes MDP—L—Ala—glyceryl—mycolate | 100 | 16 | 11 | 10 | 44 |

These results show that the protection by liposome, under the conditions of the experiment, of the products according to the invention is a function of the moment at which they are administered with respect to the infection. They also show that administration in liposome form is capable of generating a non-negligible protection under the conditions for which the product administered in solution does not manifest anti-Listeria activity.

We claim:

1. A compound which is an immunological adjuvant and effective against Klebsiella, which compound has the formula:

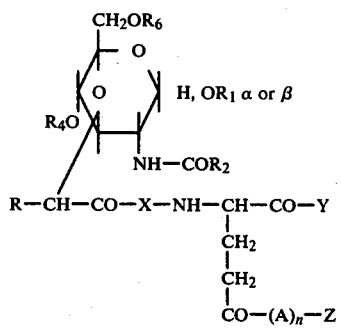

in which the substituents R, $R_1$, $R_2$, $R_4$, $R_6$, X, Y and Z has the following definition:
 R is hydrogen or an alkyl group having 1 to 4 carbon atoms,
 $R_1$ is hydrogen hydroxyl or phenylamino,
 $R_2$ is hydrogen or methyl,
 $R_4$ is hydrogen or acyl group having 1 to 4 carbon atoms, $R_6$ is hydrogen, saturated or unsaturated acyl having from 1 to about 4 carbon atoms, mycolyl group having 80 to 90 carbon atoms or corynomycoyl, X is L-alanyl, L-seryl, L-valyl, or glycyl, Y is -OH, an alkoxy radical having from 1 to 10 carbon atoms, or -$NH_2$, the hydrogens of the amino group being optionally substituted by alkyl residues having 1 to 10 carbon atoms, or an aminoacyl residue, A is an aminoacyl residue selected from the group consisting of L-alanyl, L-arginyl, L-asparagyl, L-aspartyl, L-cystenyl, L-glutaminyl, L-glutamyl, glycyl, L-histidyl, L-hydroxyprolyl, L-isoleucyl, L-leucyl, L-lysyl, L-methionyl, L-orinthyl, L-phenylalanyl, L-prolyl, L-seryl, L-threonyl, L-tryptophanyl, L-tyrosyl and L-valyl or an aminoalcohol residue (-NH-CH-$CH_2$-O-) corresponding to these aminoacyls (-NH-CH-CO-), wherein when the A groups are present in the same compound they may be identical or different, n is zero or 1, Z is selected from the group consisting of -OR', -NHR', -O$CH_2$-$CH_2$O-COR' or -O$CH_2$-CHOH-$CH_2$O-R°, wherein R° is a mycolic acid group having from 80 to 90 carbon atoms, or corynomycoyl and R' is a linear or branched alkyl group having 4 to 20 carbon atoms.

2. The compound according to claim 1, wherein X is the L-alanyl residue.

3. The compound according to claim 1 wherein Z is -O$CH_2$-CHOH-$CH_2$O-R°, wherein R°, is a mycolic acid group having from 80 to 90 carbon atoms or corynomycolyl.

4. The compound according to claim 1, wherein A is L-alanyl.

5. The compound according to claim 1, wherein Y is -OH.

6. The compound according to claim 1, wherein Y is -O$CH_3$.

7. The compound according to claim 1, wherein Y is -O$C_4H_9$.

8. The compound according to claim 1, wherein Y is -$NH_2$.

9. The compound according to claim 1, wherein R is hydrogen.

10. The compound according to claim 1, wherein R is -$CH_3$.

11. The compound according to claim 1, wherein $R_1$, $R_4$ and $R_6$ are hydrogen.

12. The compound according to claim 1, wherein $R_1$, $R_6$ is selected from the group consisting of hydrogen, acetyl and succinyl.

13. The compound according to claim 12, wherein $R_6$ is hydrogen.

14. The compound according to claim 13 wherein A is L-alanyl.

15. The compound according to claim 14 wherein Y is amine.

16. The compound according to claim 1, wherein $R_6$ is acyl of 1 to 4 carbon atoms.

17. The compound according to claim 1 wherein R' is an alkyl group having 15 to 20 carbon atoms.

18. A compound which has anti-Listeria activity, which compound has the formula

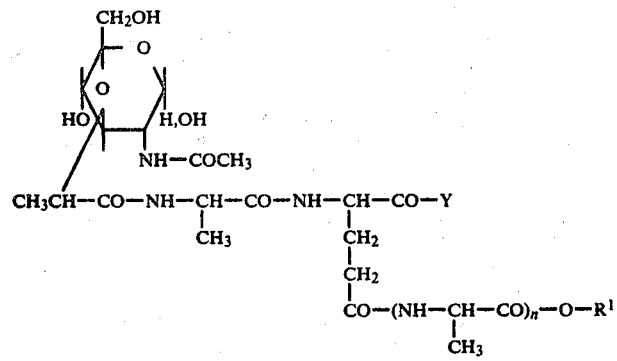

wherein

Y is selected from the group consisting of hydroxy, amino and alkoxy of 1 to 10 carbon atoms, and $R^1$ is a linear or branched alkyl group having 4 to 20 carbon atoms or -O$CH_2$-OCHOH-$CH_2$O-R°, wherein R° a mycolic acid group having from 80 to 90 carbon atoms.

19. The compound of claim 18 wherein R' is alkyl of 4 to 10 carbon atoms.

20. The compound of claim 18 wherein Y is an alkoxy of 3 to 5 carbon atoms.

21. The compound of claim 18 wherein Y is butoxy and R' is decyl.

22. The compound of claim 18 wherein Y is amino, n is 0 and R' is butyl.

23. The compound of claim 18 wherein Y is amino, n is 1 and R' is butyl.

24. The compound of claim 18 wherein Y is propoxy, n is 0 and $R_1$ is butyl.

25. The compound of claim 18 wherein Y is propoxy, n is 1 and R' is butyl.

26. The compound of claim 18 wherein Y is pentoxy, n is 0 and R' is butyl.

27. The compound of claim 18 wherein Y is pentoxy, n is 1 and R is butyl.

28. The compound of claim 18 wherein Y is amino, n is 0 and R' is -O$CH_2$-CHOH-$CH_2$O-R°, wherein R° is a mycolic acid group having 80 to 90 carbon atoms.

29. The compound of claim 18 wherein Y is ethoxy, n is zero and R is decyl.

30. A pharmaceutical composition for stimulating the immune response in warm-blooded animals, which comprises a biologically acceptable carrier and an effective dose of at least one effective compound of claim 1.

31. The pharmaceutical composition according to claim 30, wherein the lipid portion of the liposomes have a lipid portion.

32. The pharmaceutical composition according to claim 31 wherein the lipid portion of the liposomes is constituted by a phospholipid.

33. The pharmaceutical composition according to claim 32 wherein the compound is N-acetyl-muramyl-L-alanyl-D-isoglutaminyl-L-alanyl-D-glyceryl-mycolate.

34. The pharmaceutical composition according to claim 30 wherein the aqueous phase is buffered to a pH at or near neutrality.

35. The pharmaceutical composition according to claim 30, wherein the injectable medium is constituted by an aqueous injectable isotonic and sterile saline or glucose solution.

36. The pharmaceutical composition according to claim 30, wherein the active compound is suitable for oral administration.

37. The pharmaceutical composition according to claim 36 wherein the compound is N-acetyl-muramyl-l-alanyl-D-isoglutaminyl-L-alanyl-butyl ester.

38. The pharmaceutical composition according to claim 36 wherein the compound is N-acetyl-muranyl-L-alanyl-D-isoglutaminyl-butyl ester.

39. The pharmaceutical composition according to claim 30 for anti-infectious treatment and parenteral administration, in the form of unit doses containing from 10 to 20,000 mg of the effective compound.

40. A biological composition for stimulating in a warm-blooded animal an immune response against Listeria comprising a biologically acceptable carrier and an effective dose of at least one compound of claim 18, 19, 20, 21, 22, 23, 24, 25, 27, 28 or 29.

41. A method for modifying the immune responses of a warm blooded animal comprising administering to said warm-blooded animal a composition comprising a biologically acceptable carrier and an effective amount of at least one compound of claim 1.

42. The method according to claim 41 wherein the compound is administered orally.

43. A method for treating infectious diseases in warm-blooded animals comprising administering an effective amount of at least one compound of claim 1 to said animal.

44. The method according to claim 43 wherein the compound administered is N-acetyl-muramyl-alanyl-D-isoglutaminyl-L-alanyl-butyl ester.

45. The method according to claim 43 wherein the compound is N-acetyl-muranyl-L-alanyl-D-isoglutaminyl-butyl ester.

46. A method of stimulating an immune response in a warm-blooded animal against Listeria which comprises administering to said animal a composition comprising a biologically acceptable carrier and an effective amount of at least one compound of the formula of claim 18, wherein Y is selected from the group consisting of hydroxy, amino and alkoxy of 1 to 10 carbon atoms, and $R_1$ is a linear or branched alkyl group having 4 to 20 carbon atoms or $-OCH_2-CHOH-CH_2O-R°$, wherein R° is a mycolic acid group having from 80 to 90 carbon atoms.

47. The method of claim 46 wherein the compound is N-acetyl-muramyl-L-alanyl-D-isoglutaminyl-L-acyl-D-glyceryl-mycolate, wherein the mycolic acid radical contains from 80 to 90 carbon atoms.

48. The method of claim 47 wherein the compound is N-acetyl-murmyl-L-alanyl-D-isoglutaminyl-butyl ester.

49. A method for producing a delayed type hypersensitivity reaction to antigens in warm-blooded animals which comprises administering to said animal an effective amount of the compound of claim 18 and a biologically acceptable carrier.

* * * * *